(12) United States Patent
Taylor

(10) Patent No.: US 8,070,816 B2
(45) Date of Patent: Dec. 6, 2011

(54) ARTHROPLASTY SPINAL PROSTHESIS AND INSERTION DEVICE

(75) Inventor: Brett Allison Taylor, Clayton, MO (US)

(73) Assignee: 3HBFM, LLC, Dayton, OH (US)

( * ) Notice: Subject to any disclaimer, the term of this patent is extended or adjusted under 35 U.S.C. 154(b) by 1391 days.

(21) Appl. No.: 10/810,610

(22) Filed: Mar. 29, 2004

(65) Prior Publication Data

US 2005/0216081 A1 Sep. 29, 2005

(51) Int. Cl.
*A61F 2/44* (2006.01)
(52) U.S. Cl. ............... 623/17.15; 623/17.14; 623/17.11; 623/17.16
(58) Field of Classification Search ............. 606/61
See application file for complete search history.

(56) References Cited

U.S. PATENT DOCUMENTS

| | | | | |
|---|---|---|---|---|
| 4,932,975 A * | 6/1990 | Main et al. | | 623/17.12 |
| 5,002,576 A | 3/1991 | Fuhrmann et al. | | 623/17 |
| 5,258,031 A * | 11/1993 | Salib et al. | | 623/17.15 |
| 5,360,430 A | 11/1994 | Lin | | 606/61 |
| 5,425,773 A | 6/1995 | Boyd et al. | | 623/17 |
| 5,458,642 A | 10/1995 | Beer et al. | | 623/17 |
| 5,534,029 A * | 7/1996 | Shima | | 623/17.15 |
| 5,554,191 A | 9/1996 | Lahille et al. | | 623/17 |
| 5,556,431 A | 9/1996 | Büttner-Janz | | 623/17 |
| 5,562,738 A | 10/1996 | Boyd et al. | | 623/17 |
| 5,653,763 A | 8/1997 | Errico et al. | | 623/17 |
| 5,674,296 A | 10/1997 | Bryan et al. | | 623/17 |
| 5,755,796 A | 5/1998 | Ibo et al. | | 623/17 |
| 5,827,328 A * | 10/1998 | Buttermann | | 623/17.13 |
| 5,865,846 A | 2/1999 | Bryan et al. | | 623/17 |
| 6,001,130 A | 12/1999 | Bryan et al. | | 623/17 |
| 6,063,121 A | 5/2000 | Xavier et al. | | 623/17 |
| 6,102,950 A | 8/2000 | Vaccaro | | 623/17 |
| 6,113,637 A * | 9/2000 | Gill et al. | | 623/17.15 |
| 6,146,421 A | 11/2000 | Gordon et al. | | 623/17.15 |
| 6,156,067 A | 12/2000 | Bryan et al. | | 623/17.15 |
| 6,190,413 B1 | 2/2001 | Sutcliffe | | 623/17.11 |
| 6,228,118 B1 | 5/2001 | Gordon | | 623/17.14 |
| 6,296,643 B1 * | 10/2001 | Hopf et al. | | 606/61 |
| 6,368,350 B1 * | 4/2002 | Erickson et al. | | 623/17.14 |
| 6,375,682 B1 | 4/2002 | Fleischmann et al. | | 623/17.12 |
| 6,395,031 B1 | 5/2002 | Foley et al. | | 623/17.11 |

(Continued)

FOREIGN PATENT DOCUMENTS

EP 1344507 A1 9/2003

(Continued)

OTHER PUBLICATIONS

English translation of Japanese Office Action for Application No. 2007-506427 mailed on Nov. 16, 2009.

(Continued)

*Primary Examiner* — Thomas J Sweet
*Assistant Examiner* — Christopher D Prone
(74) *Attorney, Agent, or Firm* — Dorsey & Whitney LLP

(57) ABSTRACT

An arthroplasty spinal prosthesis with first and second vertebra contacting members that are configured for engaging opposing vertebrae An articulation is supportively associated with the contacting members to allow relative pivotal and translational motion therebetween over anterior-posterior and lateral pivotal axes, and over anterior-posterior and lateral translational axes. This motion allows the opposing vertebrae to pivot and translate with respect to each other. The articulation is configured to permit translational movement substantially uncoupled from the pivoting movement.

29 Claims, 23 Drawing Sheets

U.S. PATENT DOCUMENTS

| | | | |
|---|---|---|---|
| 6,517,580 B1 | 2/2003 | Ramadan et al. | 623/17.15 |
| 6,749,635 B1 * | 6/2004 | Bryan | 623/17.16 |
| 6,770,095 B2 * | 8/2004 | Grinberg et al. | 623/17.14 |
| 2002/0004683 A1 | 1/2002 | Michelson | 623/17.16 |
| 2002/0035400 A1 | 3/2002 | Bryan et al. | 623/17.15 |
| 2002/0099444 A1 | 7/2002 | Boyd et al. | 623/17.16 |
| 2002/0128715 A1 | 9/2002 | Bryan et al. | 623/17.15 |
| 2002/0143399 A1 | 10/2002 | Sutcliffe | 623/17.11 |
| 2002/0183761 A1 * | 12/2002 | Johnson et al. | 606/90 |
| 2004/0133278 A1 * | 7/2004 | Marino et al. | 623/17.14 |
| 2005/0060034 A1 * | 3/2005 | Berry et al. | 623/17.11 |

FOREIGN PATENT DOCUMENTS

| | | |
|---|---|---|
| JP | 6-7391 | 6/1994 |
| JP | 2002143192 | 5/2002 |
| WO | WO 00/35383 | 6/2000 |
| WO | WO 00/35386 | 6/2000 |
| WO | WO 02/089701 | * 11/2002 |

OTHER PUBLICATIONS

Official Decision of Grant for Application No. 2007-506427 mailed on Jun. 8, 2010.

* cited by examiner

ARTHROPLASTY SPINAL PROSTHESIS AND INSERTION DEVICE

FIELD OF THE INVENTION

The present invention relates to a prosthesis for articular association with the bone structure of a patient, and more particularly to a spinal prosthesis.

BACKGROUND OF THE INVENTION

Procedures exist for replacing diseased intervertebral disks in which the disk material is typically removed from between adjacent vertebral bodies, and the adjacent bodies are fused. This has been done with a cage filled with bone or bone forming proteins placed in between the bodies to fix them to each other, generally to support and promote fusion between the adjacent vertebrae.

In arthroplastic procedures, a pivotally articulated prosthesis is implanted between the vertebrae in the site of the diskectomy. For example, U.S. Pat. Nos. 5,425,773 and 6,063,121 disclose intervertebral arthroplasty devices that use different ball and socket arrangements to permit movement between the vertebrae. The ball and socket is disposed at center between surfaces of plates that are placed against the vertebrae. The intervertebral disk prosthesis disclosed in U.S. Pat. No. 5,556,431 has a core and endplates with a spherical articular surface. The core has an edge rim that limits the range of movement.

Other teachings also provide for translational movement between the vertebrae. U.S. Pat. No. 6,113,637, for instance, shows an intervertebral joint with a ball component engaged with a vertebra and with a trough component, which is engaged with another vertebra. The trough component has a flat portion that allows translation of the ball component on one axes. A prosthesis disclosed in Patent Application Publication U.S. 2002/0128715 shows a flexible central body between two rigid opposing shells to allow combined translation and bending.

There is a need for an improved disk prosthesis that provides improved articulation between the vertebrae between which it is implanted.

SUMMARY OF THE INVENTION

The present invention relates to an arthroplasty spinal prosthesis for implantation in a human or animal to provide improved implantation longevity and articulation kinematics similar to the tissue being replaced. The preferred embodiment of the prosthesis has first and second bone or vertebra contacting members configured for engaging opposite articulated bones, preferably bones of the axial skeleton, such as two vertebrae or a vertebra and the skull. An articulation is supportively associated with the contacting members to allow relative pivotal and translational movement therebetween. This movement is preferably over anterior-posterior and lateral pivotal axes and over anterior-posterior and lateral translational axes. The movement between the contacting members allows the opposing vertebrae to pivot and translate with respect to each other. Also, the preferred articulation is configured to permit the translational movement to occur without coupling or causing a pivotal movement, although another embodiment can provide the coupling if desired. Preferably, the amount of translational or pivotal movement is substantially not affected or dependent on the other of these movements. Thus, the contacting members can translate regardless of whether they also pivot, and they can pivot regardless of whether they may also translate. Similarly, the preferred articulation allows the contacting members to rotate axially with respect to each other, and this rotation is also not substantially coupled by the articulation with the pivotal or translational movement. Preferably, the prosthesis also allows synchronous movements of flexion and translation as well as movement simultaneously in rotation bending, and flexion/extension.

The preferred articulation is configured for limiting the translational movement along both translational and pivotal axes to within predetermined ranges. The preferred translational axes extends substantially through at least one of the pivotal axes, and most preferably both anterior-posterior and lateral translational axes extend substantially through both anterior-posterior and lateral pivotal axes, with regard to one or both contacting members.

Preferably, the articulation has first and second articulation portions that are moveably associated with each other. The first articulation portion is pivotally associated with the first contacting member, and the second articulation portion is pivotally associated with the second contacting member. The first articulation portion or first contacting member can define a protrusion, while the other defines a recess configured to receive the protrusion to pivotally associate these two elements. A similar structure with a protrusion and recess can also be provided for the second articulation portion and second contacting member. At least one of the recess and protrusion is preferably tapered substantially about a spinal axes that extends axially between the connecting members. The articulation portions also preferably comprise blocking members that are juxtaposed radially with respect to the spinal axes to abut each other for limiting the translational movement between the articulation portions to provide semiconstrained translation. The blocking members can include a key that extends from one articulation portion and that fits into a keyway defined in the other articulation portion. The association between the key and keyway allows translational movement, and the keyway provides an edge wall disposed to block the translational movement of they key. Preferably, the edge wall substantially surrounds the key, and both the edge wall and key are annular about the spinal axes. Most preferably, the edge wall comprises two edge walls that are disposed on opposite sides of the keyway so that the key and edge wall concurrently contact each other at least two locations to block the translational movement. In one embodiment, the key and keyway can have a dovetail configuration or cross-section to axially retain the key within the keyway at a limit of the translational travel.

The preferred articulation portions are ring shaped with a hollow center. A retaining member can be associated with the contacting members to extend through the hollow center of the articulation portions to prevent the escape of the articulation portions, such as when subjected to extreme trauma. The retaining member can comprise, for example a suture or other flexible material or a post extending through the hollow center of at least one of the articulation portions. Suture openings can be provided through the contacting members and any structures therebetween to allow the suture to extend from one contacting member to the other and to be fastened thereabout.

The first and/or second contacting members of the preferred embodiment include a fastener mount portion that is configured to attach a bone fastener from the prosthesis to the vertebra that is engaged therewith. Vertebral contacting surfaces of this contacting member are disposed and oriented to position the body of the engaged vertebra such that the apophyseal ring of the body is disposed with respect to the fastener mount portion in an attachment position for attaching the fastener from the fastener mount portion through the apophyseal ring. The fastener mount portion can define an opening to receive a threaded surgical fastener, such as a surgical screw, and which can be made of metal, polymer, or absorbable material. The preferred fastener mount portion is oriented for inserting the fastener diagonally into the apophyseal ring. Also, a plurality of fastener mount portions can be provided to insert a plurality of fasteners through the apophyseal ring. Additional fastener mount portions can be provided to insert other fasteners in other orientations and locations into the vertebra, such as oblongly or laterally, which can be beneficial for use in different parts of the spine, for instance with L1 or L2 vertebrae.

The vertebral contacting surfaces of the preferred embodiment are oriented to capture axial and radial surfaces of the vertebral body to position the apophyseal ring in the attachment position. The axial contacting surface is preferably oriented to abut and support an axial face of the vertebral body, while the radial contacting surface is preferably configured to abut a radial side of the vertebral body. An apophysis grove can be defined between the axial and radial contacting surfaces to receive the apophyseal ring. A fastener mount portion is preferably configured to direct the fastener into the apophysis grove, to ensure that the fastener penetrates the apophyseal ring.

An embodiment of the prosthesis has at least one of the contacting members and articulation that is made of radiolucent material to reduce or avoid creating an artifact on an MRI, computed tomography or an x-ray or otherwise significantly obscure or block an image being produced. Preferably, the entire prosthesis, and at least major portions thereof, such as the contacting members and articulation and optionally the fasteners, are substantially radiolucent. Radiopaque markings can be provided that are visible on an MRI, an x-ray, a CT scan, or other imaging systems to help displace and position the prosthesis during implantation, or to monitor its position thereafter. The prosthesis can be configured to deliver a treatment, such as by comprising and delivering an antibiotic, protein, or biologically active substance to the implantation site. This substance can be impregnated in the material of one or both of the contacting members. Polymethylmethacrylate (PMMA) can be used for a slow release of the substance.

Some embodiments of the inventive prosthesis have a vertebral body prosthetic portion that is configured to replace at least a portion of a vertebral body of the patient. The body prosthetic portion is fitted between the contacting members and is articulably associated therewith via articulations, such as the articulation portions described. Consequently, this prosthesis has portions configured to replace both at least a portion of a vertebral body and two adjacent disks. This prostheses can be used in an implantation site between two nonadjacent vertebrae, and is preferably configured to carry the spinal loads through the contacting members, articulations, and vertebral body portion when implanted.

A preferred prosthesis insertion device includes first and second holding portions that have a holding position in which the holding portions cooperatively and positively hold the prosthesis. A connecting member is associated with the holding portions to selectively maintain the holding portions in the holding position and for releasing them therefrom. In the holding position, the holding portions cooperatively capture the prosthesis sufficiently to prevent removal thereof from the holding portions and to maintain a predetermined orientation between the articulated portions of the prosthesis, such as the contacting member. When released from the holding position, the holding portions are configured to release the prosthesis.

Preferably, the connecting member comprises a hinge that pivotally connects the holding portions. This hinge can be part of a scissor linkage for moving the holding portions to and from the holding position. Alignment bores can be provided in the holding portions, including bores formed cooperatively by aligning groves in each holding portion when they are placed in the holding position. These bores can be configured for guiding a drill, such as by inserting a drill guide therein, or for guiding a fastener or fastener driver to a predetermined position and orientation with respect to the prosthesis.

The present invention thus provides an improved prosthesis and implantation device for use in the spinal column with improved wear and articulation characteristics.

DETAILED DESCRIPTION OF THE PREFERRED EMBODIMENTS

Figure 1:
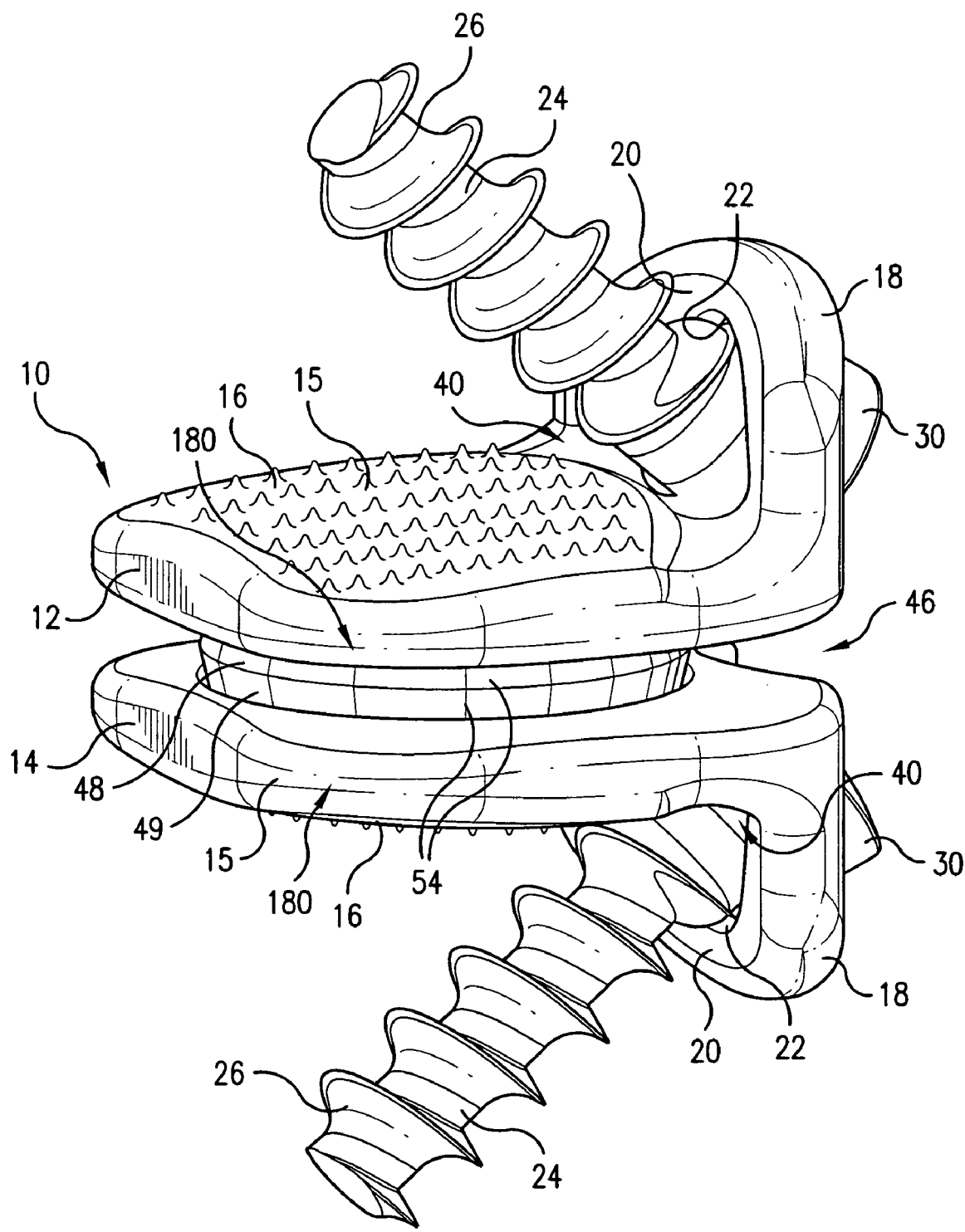
FIGS. 1-3 are perspective, exploded, and side cross-sectional views, respectively, of a preferred embodiment of an intervertebral disk prosthesis constructed according to the present invention.
Figure 2:
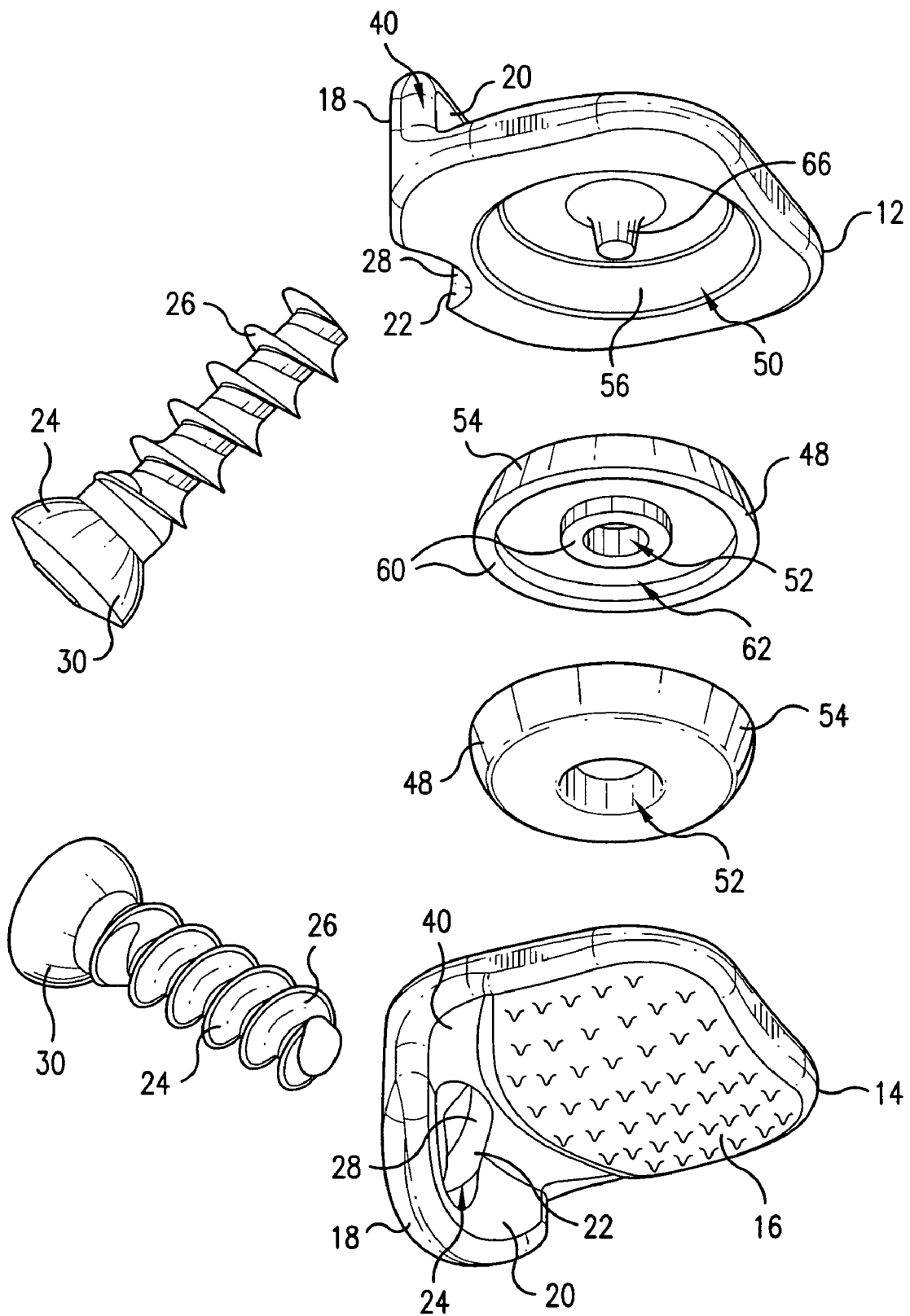
Figure 3:
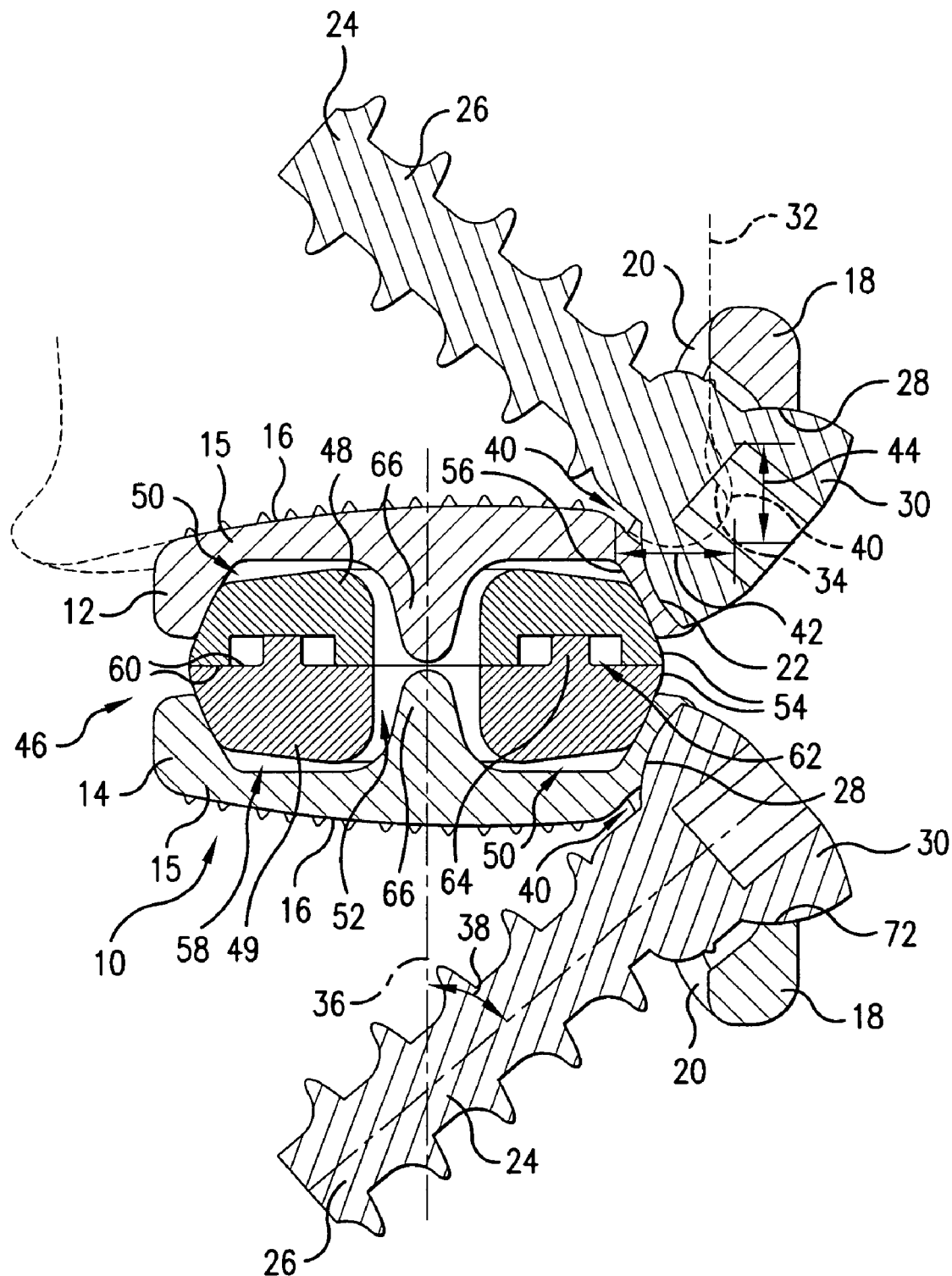

Referring to FIGS. 1-3, the preferred embodiment of the invention is a vertebral disk prosthesis 10, which includes top and bottom contacting members 12,14. The contacting members 12,14 preferably include top and bottom endplates. Each contacting member 12,14 of this embodiment has a main body support portion 15 that includes an axial vertebral contacting surface 16 facing axially and configured for engaging axial superior or inferior faces of opposing vertebral bodies when implanted along a spinal column.

The vertebral contacting surfaces 16 preferably have a texture, shape, and/or treatment to promote engagement with the face of the engaged vertebral body. The texture shown provides an uneven surface to improve gripping against the vertebral body and to promote bone ingrowth into the surfaces 16. The uneven surface can include a series of angular or pointed shapes or other protrusions and indentations, such as pyramids, scales, or tetrahedrons, or trebecular metal for example. Alternatively or additionally, the axial contacting surfaces 16 can have other surface treatments, and can be coated, for instance, with plasma sprayed titanium, calcium phosphate, hydroxyapetite, or proteins. In some embodiments, the surfaces can be smooth.

The uneven surface is preferably disposed to engage and grip the concave interior portion of the axial face of the vertebral body, most preferably within the apophyseal ring. To best engage this interior portion, the axial contacting surfaces 16 are preferably convex and curved along one or two radial directions, preferably along an anterior-posterior direction and a lateral direction. The contacting surface preferably has an overall rounded shape to prevent expulsion and increase contact. The rounded shape can improve and provide immediate stability to prevent expulsion.

The contacting members 12,14 also preferably include flanges 18 that extend axially at an angle to the axial vertebral contacting surfaces 16 and include radial vertebral contacting surfaces 20. The radial contacting surfaces 20 are preferably oriented to abut the radial wall of the vertebra body. Most preferably, the radial contacting surfaces 20 are concave to follow the shape of the radial wall. In a preferred embodiment, the flanges 18 are disposed and configured to contact the front radial side of the vertebral body, but in an alternative embodiment, the flanges 18 and radial contacting surfaces can be oriented to contact another radial side of the vertebral body, such as a lateral side or a portion partway between a lateral side and the anterior or posterior side, such as at an oblique side of the wall.

A fastener mount portion 22 is preferably provided for attaching a bone fastener 24 thereto, such as a bone screw or other bone fastener. The fastener mount portion 22 preferably defines an opening 24 to receive a threaded portion 26 of the fastener 24 for insertion into the vertebra, and has a fastener seat 28 to align and seat a head 30 of the fastener 24.

The contacting surfaces 16,20 are disposed and oriented to position the vertebral body to be engaged with the prosthesis 10 to position apophyseal ring of the body in an attachment position with respect to the fastener mount portion 22. In the attachment position, shown in FIG. 3, the apophyseal ring 34 of the vertebral body 32, shown in phantom lines, is disposed with respect to the fastener mount portion 22, such that the fastener 24 is aligned to extend through the apophyseal ring 34 to attach the contacting members 12,14 to the vertebra 32. This positioning of the fastener is desired since the apophyseal ring 24 is the strongest part of the vertebral body and it ensures a strong, robust and immediate attachment of the prosthesis 10 to the vertebra 32. The fastener 24 preferably extends diagonally into the apophyseal ring, preferably at an angle 38 of at least about 10°, more preferably at least about 30°, and most preferably at least about 40° with respect to the spinal axes 36; and preferably at most about 80°, more preferably at most about 60°, and most preferably at most about 50° thereto.

The contacting surfaces 16,20 of the contacting members 12,14 also preferably define a apophysis groove 40 defined between the axial and radial contacting surfaces 16,20 to receive the apophyseal ring 34. The apophysis groove 40 has a curvature around the spinal axes 36 configured to follow the general shape of the apophyseal ring 34. The dimensions of the apophysis groove 40 are selected to receive the apophyseal ring 40 therein so that the axial and radial contacting surfaces 16,20 can abut the axial and radial surfaces of the vertebral body 32. The fastener mount portion 22 is preferably disposed with the opening 24 extending into the apophysis groove 40 to direct the fastener 24 into the apophysis groove 40 as well.

Although the apophysis groove 40 can be made to extend into only the axial or the radial contacting surface 16 or 20, in the preferred embodiment, the apophysis groove extends into both the axial and radial contacting surfaces 16,20. The radial width 42 and axial height 44 of the apophysis groove 40 are preferably between about 2 mm and 5 mm, and more preferably between about 2.5 mm and 4 mm. The height and width can have the same or different dimensions from each other. Most preferably, the height 44 of the apophysis groove 40 is sufficient to position the apophyseal ring 34 to extend vertically within the groove 40 in the flange 18 at least up to about half the height of the fastener 24 to ensure the fastener 24 transects the apophyseal ring 34. In the preferred embodiment, the apophysis groove 40 is configured so that its surface abuts and supports the apophyseal ring 34, although in another embodiment, the apophysis groove 40 provides a clearance from the apophyseal ring 34. The dimensions of groove 40 can be selected to move the center of rotation posteriorly in the disk space. Preferably, the axial and radial contacting surfaces 16,20 are oriented to capture axial and radial surfaces of the vertebral body 32 for positioning the apophyseal ring in the attachment position.

The prosthesis 10 includes an articulation 46 that articulably connects the contacting members 12,14. The articulation 46 preferably includes upper and lower articulation portions 48,49 that are received in articular cavities 50 defined on the opposite side of the main support portion 15 from the axial contacting surface 16 of each contacting member 12,14. The articulation portions 48,49 of the preferred embodiment are preferably ring shaped disks, preferably being rounded, preferably circular along a generally radial plane, with a hollow central, axial opening 52.

Outer bearing surfaces 54 of the articulation portions 48,49 are supportively associated with bearing surfaces 56 of the cavities 50. The corresponding bearing surfaces 54,56 are preferably curved in cross-section, although one set may be curved, while the abutting bearing surface is generally straight. The bearing surfaces 54,56 are configured and associated to allow the contacting members 12,14 to pivot about the articulation portions 48,49, preferably about more than one axes. When the prosthesis is loaded by supporting the adjacent vertebrae engaged therewith, a clearance 58 is preferably provided on an axial side between the articulation portions 48,49 and the contacting members 12,14. This clearance can be provided due to the axial taper of one or both of these members. The bearing surfaces 54,56, which preferably face predominantly in a radial direction but are inclined with respect to the axial and radial direction, are in supportive abutment with each other, preferably radially outside the clearance 58 area.

The articulation 46 is preferably configured to permit independent and concurrent anterior-posterior flexion and extension and lateral bending and preferably also axial rotation between the contacting members 12,14. The range of flexion/extension and lateral bend is preferably at least about 5°, more preferably at least about 8°, and most preferably at least about 10°; and is preferably up to about 20°, and more preferably up to about 16°. The pivoting is preferably limited by the abutment of edges of the contacting members 12,14, or by the articulation portions reaching the ends of possible travel within the cavities 50, although another mechanism can be provided. Other ranges can be provided for different needs in different locations of the spine.

The articulation portions 48,49 are preferably are configured to translate with respect to each other, preferably by sliding, to allow relative translation between the contacting members 12,14. Inner bearing surfaces 60 of the articulation portions 48,49 are preferably supportively and slidingly associated with each other to allow translation, preferably along more than one axes. In the embodiment shown, the inner bearing surfaces 60 are substantially planar. Preferably, one or both translational axes extend substantially through or very near the pivotal axes.

Articulation portion 48 defines a keyway channel 62 that receives a key 64, which protrudes from the inner bearing surface 60. The keyway 62 is radially wider than the key 64 by an amount selected to permit and limit the translation between the contacting members 12,14. Both the keyway 62 and key 64 are preferably annular, and most preferably circular. The key 64 and keyway 62 are preferably configured such that at the limit of the sliding travel, the key 64 and the wall of the keyway 62 abut at two points, such as at opposite ends of the respective annuli formed by the keyway 62 and key 64. Alternatively, a single point of contact can be used to block excessive translational movement. With this construction, the key 64 and keyway 62 are juxtaposed radially with respect to the spinal axes to function as blocking members.

The allowable translation can occur on more than one axes independently and simultaneously. The preferred embodiment allows anterior-posterior translation and lateral translation in ranges that are preferably about 1 mm to 2 mm for a cervical prosthesis, about 1 mm to 2.5 mm for a thoracic prosthesis, and about 2 mm to 4 mm for a lumbar prosthesis.

To prevent the articulation portions 48,49 from exiting the space between the contacting members 12,14 in a extremely traumatic event, the contacting members 12,14 have posts 66 that extend into the articular cavities 50 and axial openings 52. Under normal flexion, extension, and bending motion limits, the articulation portions 48,49 are retained in the articular cavities 50 and are prevented from escaping into the space between the radially outer edges of the contacting members 12,14 by the associated shapes of the contacting bearing surfaces 54,56. The posts 66 are most preferably configured to abut the edge of the axial openings 52 at the limit of pivotal motion, while the bearing surfaces 54,56 are also in contact.

Axial rotation between the contacting members 12,14 is preferably provided by rotational sliding between the contacting members 12,14 and the articulation portions 48,49 and/or between the articulation portions 48,49 themselves. In the preferred embodiment, the axial rotation is unlimited, and the patient's facet joints, ligaments, annulus, and tendons provide axial rotation stability.

In the preferred embodiment, the contacting members 12,14 are articulated to allow relative pivotal and translational motion therebetween over anterior-posterior and lateral pivotal axes, and also anterior-posterior and lateral translational axes. The opposing vertebrae can thus pivot and translate with respect to each other. The articulation 46 is configured to permit translational movement substantially uncoupled from the pivoting movement. Similarly, the preferred articulation allows axial rotation substantially uncoupled from the other axes of movement as well. As a result, flexion, extension, or lateral bending that is initiated in the adjacent vertebrae does not cause the articulation to induce a translation or axial rotation, for instance, and vice versa. A movement along any one axes preferably does not cause the articulation to induce a movement in another axes. This is particularly useful because normal movements in the spine can combine variable amounts of movements along different axes simultaneously or sequentially. The prosthesis 10 can thus accommodate synchronous, coupled movement and sequential movement along the spine over different axes. Additionally, due to the construction of the preferred articulation, the contacting members can have pivotal and axial-rotational axes that are displaced from each other when the articulation is in an off-center state of translation.

Figure 4:
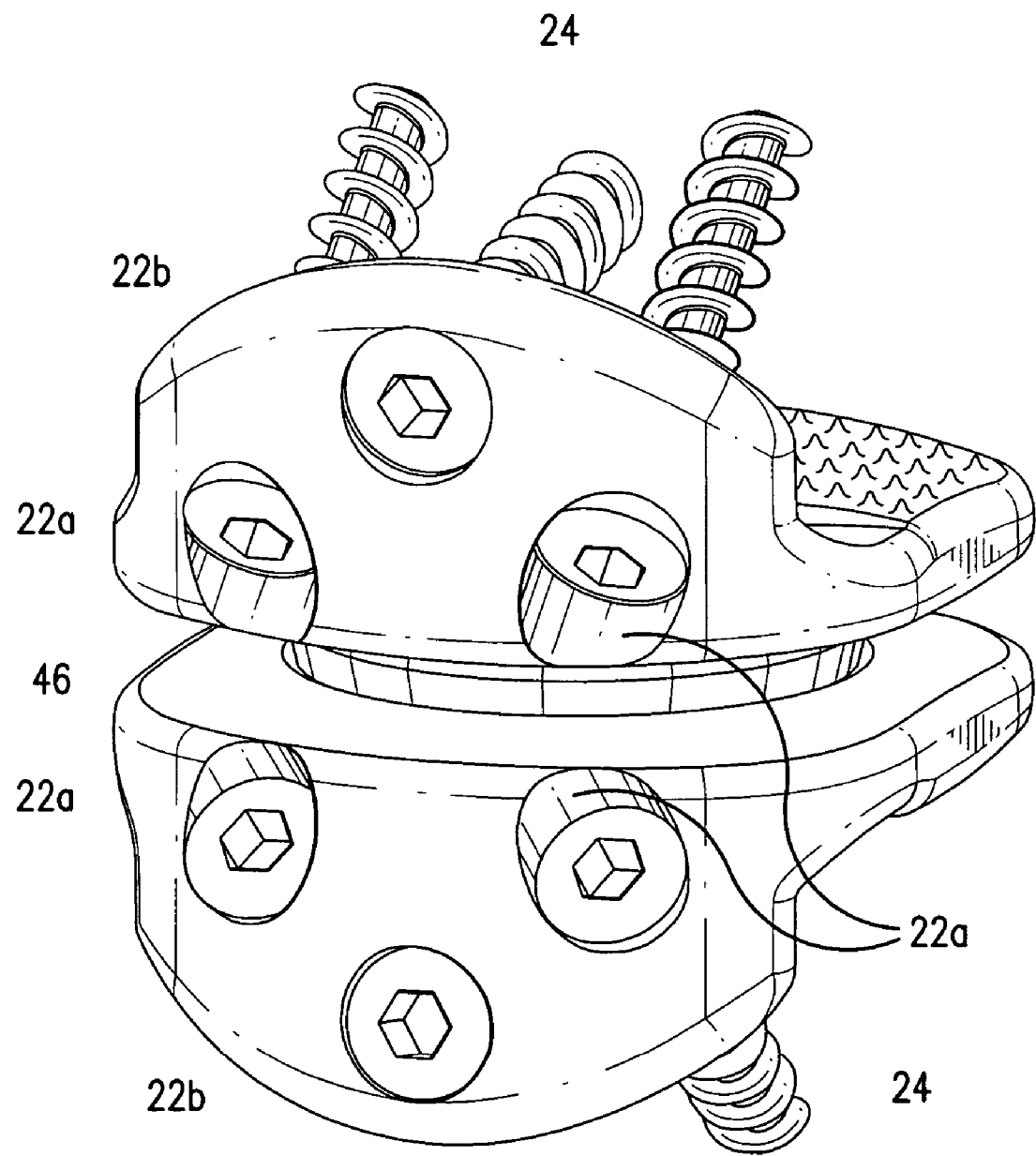
FIGS. 4 and 5 are anterior and posterior views, respectively, of another embodiment of a prosthesis with three bone-screws for fastening to each vertebra.
Figure 5:
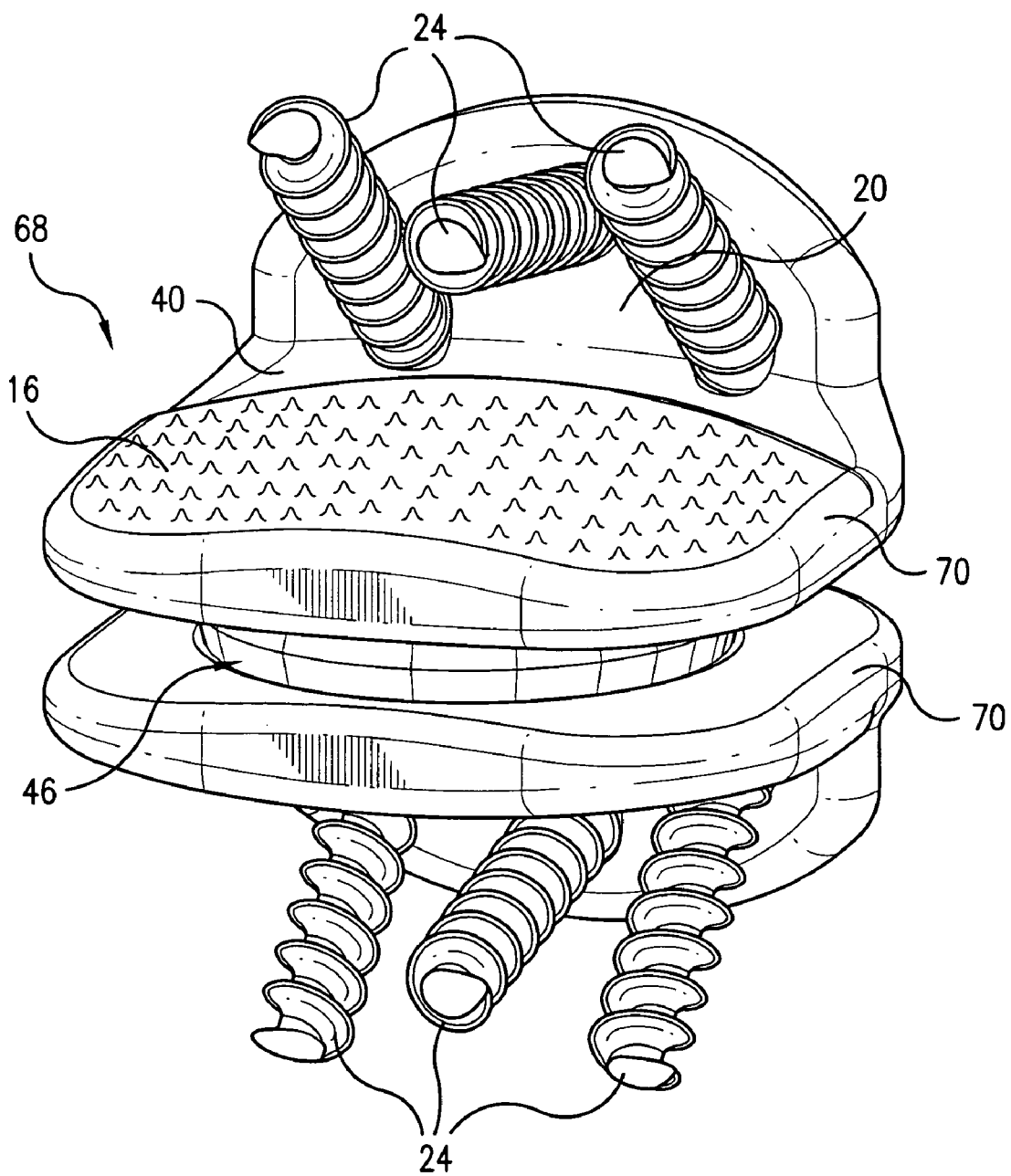

Referring to FIGS. 4 and 5, another embodiment of a prosthesis 68 has contacting members 70 with three fastener mount portions 22 on each contacting member 70. A plurality of fasteners 24 is beneficial for use with less stable or weakened bone such as with ligamentous instability, i.e., when sacrificing the posterior longitudinal ligament complex. Preferably, the majority of the fastener mount portions 22 are disposed and oriented to insert the respective fasteners 24 diagonally into the apophyseal ring. In this embodiment, fastener mount portions 22*a* have such a configuration, which fastener mounts 22*b* are configured to attach a fastener at a more horizontal angle into the vertebral body at a position above the apophyseal ring. The apophysis groove 40 shown principally extends into the axial surface 16, and by a small amount or not at all into the radial surface 20.

Figure 6:
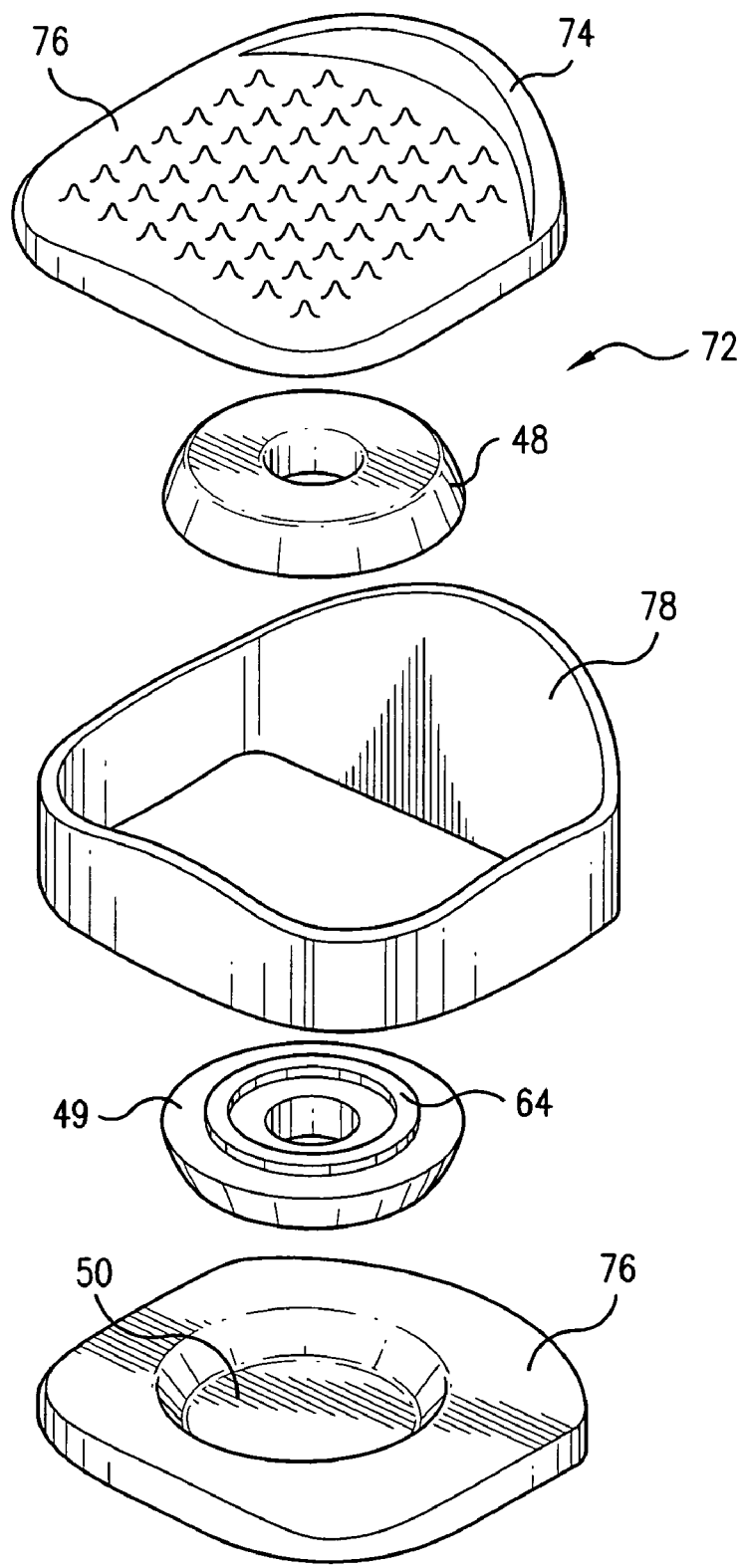
FIGS. 6 and 7 are exploded and perspective views, respectively, of another embodiment of a prosthesis that does not employ bone fasteners.
Figure 7:
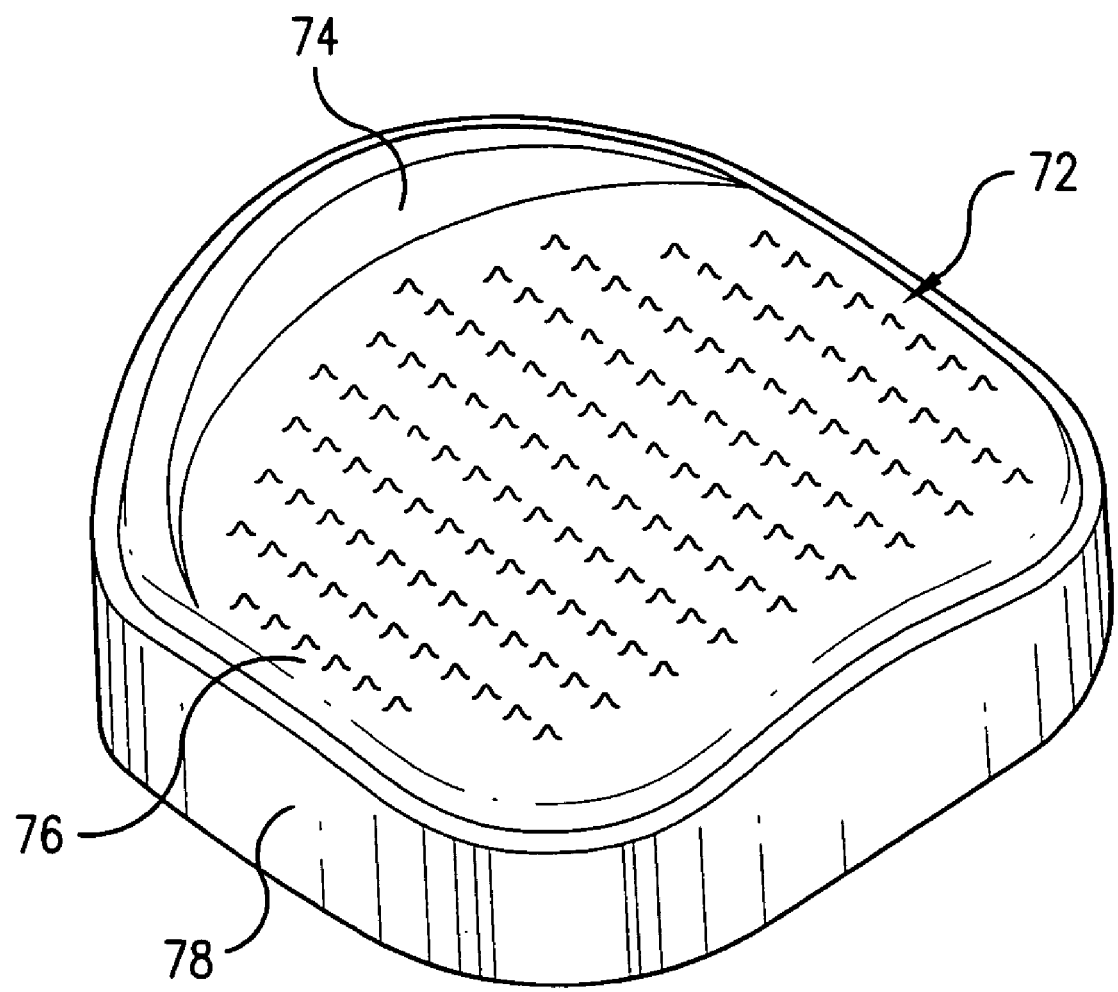

FIGS. 6 and 7 show an embodiment of a prosthesis 72 for more highly stable implantation sites, such as when sparing the posterior longitudinal ligament complex. In this embodiment, no fastener mount portions are provided. The ledges 74 of the contacting members 76 are sufficiently tall to engage the apophyseal ring of the engaged vertebral body, to prevent the prosthesis 72 from sliding further into the intervertebral space and to permit subsidence. When the ledge is implanted on the front side of the vertebral body, ledges 74 keep the prosthesis 72 from sliding towards the spinal chord. Additionally, there is no apophyseal groove provided in this embodiment, although an alternative embodiment can incorporate such a groove to positively capture the apophyseal ring.

A flexible sheath 78 is provided around the contacting members 76, preferably enclosing and optionally sealing the articular space in which the articulation portions 48,49 are disposed. The sheath 78 can advantageously resist or prevent debris from migrating from the bearing surfaces of the articulation into the body, as such debris can cause weakening of the bone. The sheath can also or alternatively be configured to resiliently bias the contacting members, such as towards a central axial rotation position. Advantageously, the periphery of the contacting members 74 can be angled to allow provide the resilient rotational bias. Other embodiments can have round contacting members, however. The membrane can also send in lubricating fluids, natural and synthetic or to provide treatments, such as antibiotics or anti inflammatory treatments. The membrane can also prevent interposition of surrounding soft tissue into the device.

Figure 8:
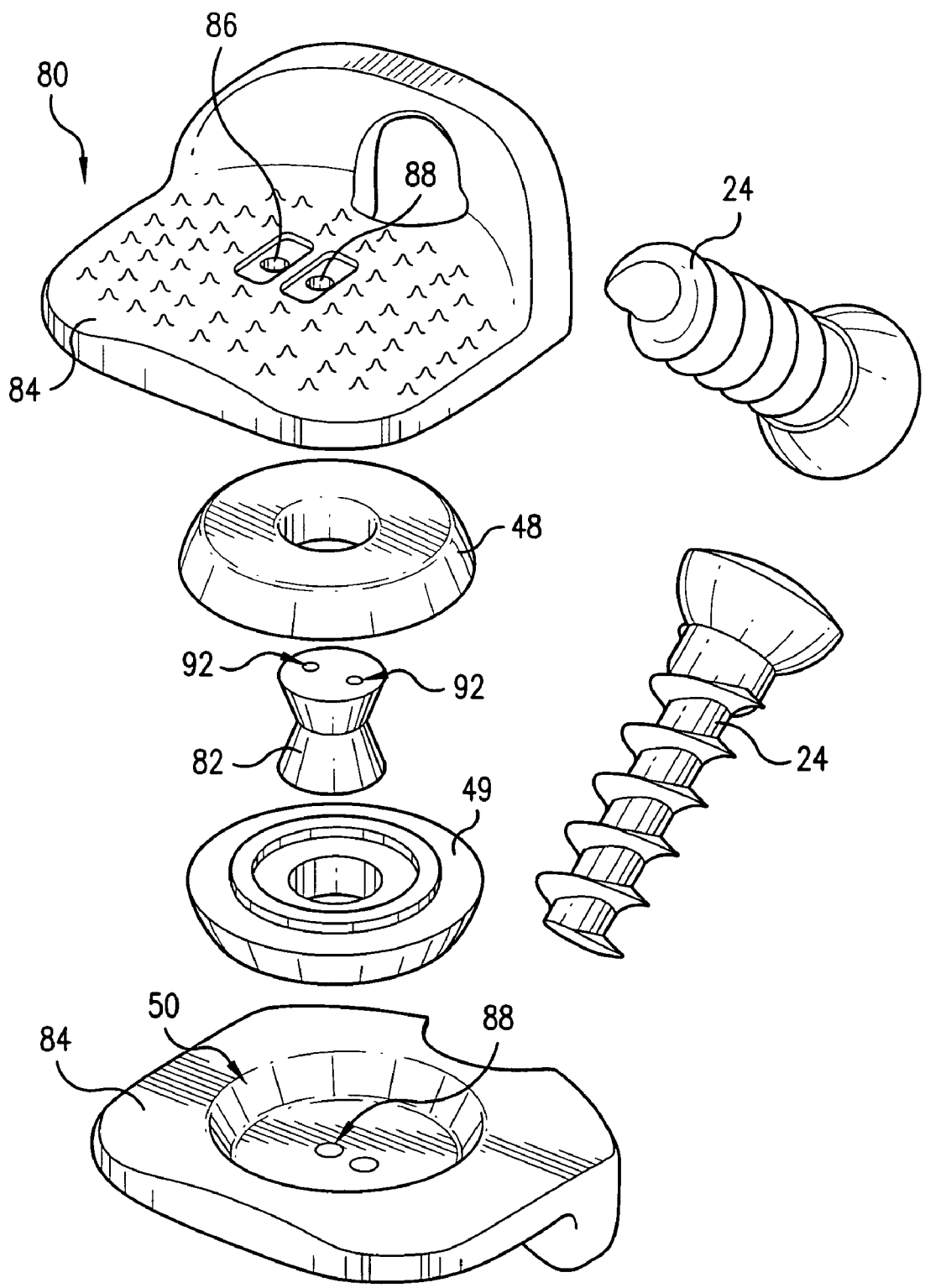
FIGS. 8 and 9 are exploded and cross-sectional views, respectively, of a prosthesis embodiment with a resilient shock-absorbing member between two vertebra contacting members.
Figure 9:
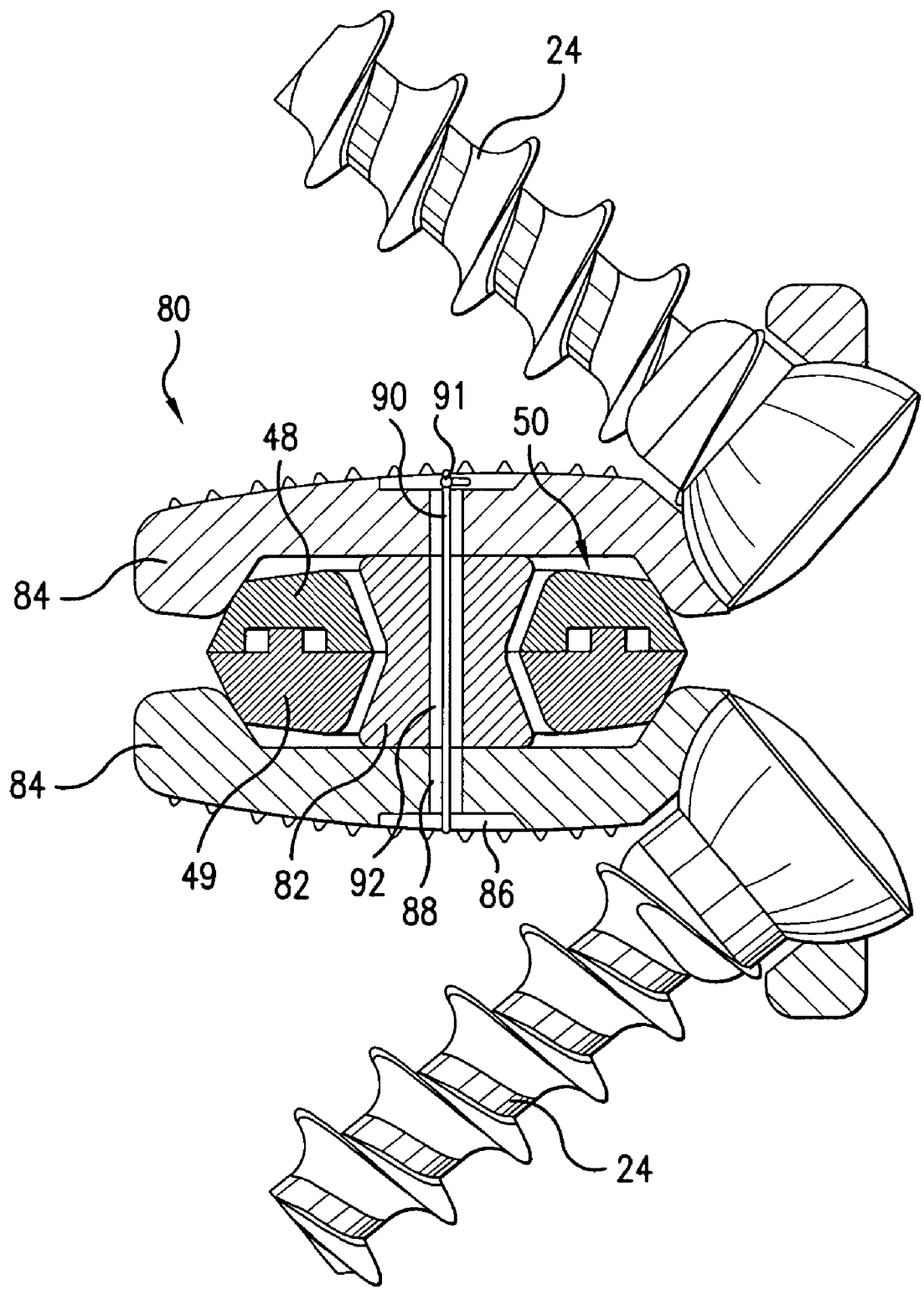

Referring to FIGS. 8 and 9, another embodiment of a prosthesis 80 does not employ posts to keep the articulation portions 48,49 from exiting the articular cavity 50. A resilient member 82 is disposed between the contacting members 84 to absorb axial shocks between the engaged vertebrae. The resilient member 82 in this embodiment has a double tapered shape, with the narrowest part at the axial center thereof to correspond with the taper of the central opening 52 in the articulation members 48,49, within which opening 52 the resilient member is preferably disposed. The resilient member is preferably made of an elastically compressible material that is significantly softer than the contacting members 84 and articulation portions 48,49. Suitable materials include elastomeric materials, including rubber and synthetic elastomers. A resilient member can also be employed with an embodiment with posts 66 to provide axial compression damping.

Suture recesses or notches 86 in which suture holes 88 are disposed are defined on the outer axial side of the contacting members 84. The suture holes 88 extend into the articular cavity 50 and are aligned with suture holes 88 of the opposing contacting member 84. A suture 90, preferably of resorbable material, can be threaded through the suture holes 88 to tie the contacting portions 84 together to retain the prosthesis 80 in an assembled condition, which is beneficial when certain ligaments have been severed for implantation, such as the annular ligament and posterior longitudinal ligament. As the tissue heals, the suture 90 can dissolve when it is no longer needed for the stability of the prosthesis 80. Alternatively, a non-dissolving suture can be used. If a central resilient shock absorbing member is employed, as shown in this embodiment, the member 82 preferably also has openings 92 through which to thread the suture 90. A different type of retaining member to retain the contacting members 84 together can alternatively be used. The notches 86 can be used for recessing the suture knot 91 or for another desired purpose, such as for anchoring a bone graft.

Figure 10:
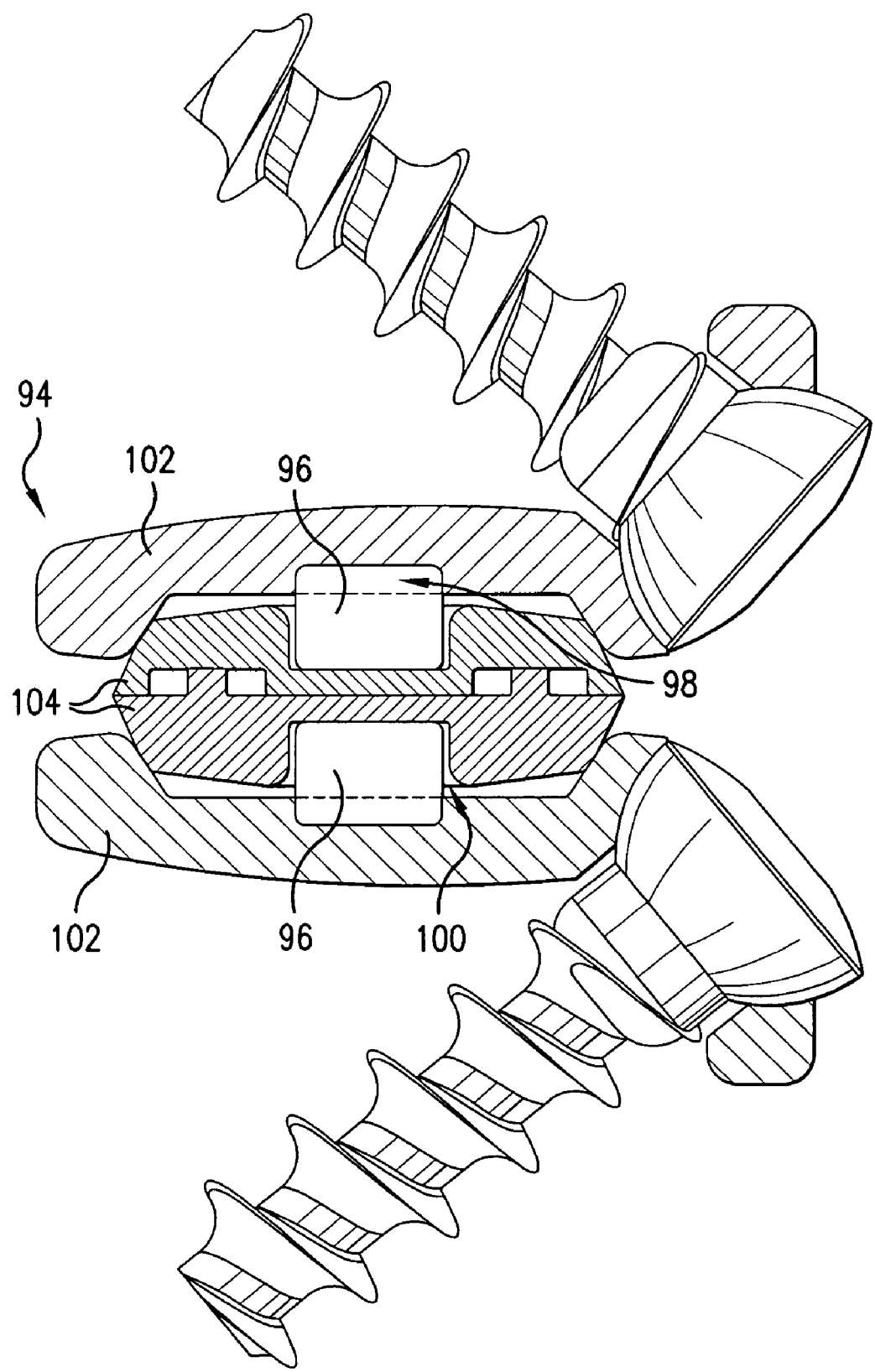
FIG. 10 is a cross-sectional view of another embodiment with upper and lower shock absorbing members.

The prosthesis embodiment 94 of FIG. 10 has resilient shock-absorber members 96 fitted in central recesses 98,100 of the contacting members 102 and articulation portions 104. In this embodiment, the articulation portions 104 have an axially closed center, not having a central opening that extends axially completely therethrough. The resilient members 96 of this embodiment can also be employed to provide a resilient bias about the anterior-posterior and lateral bending axes. A resilient shock-absorber can also be employed between the contacting members 102.

Figure 11:
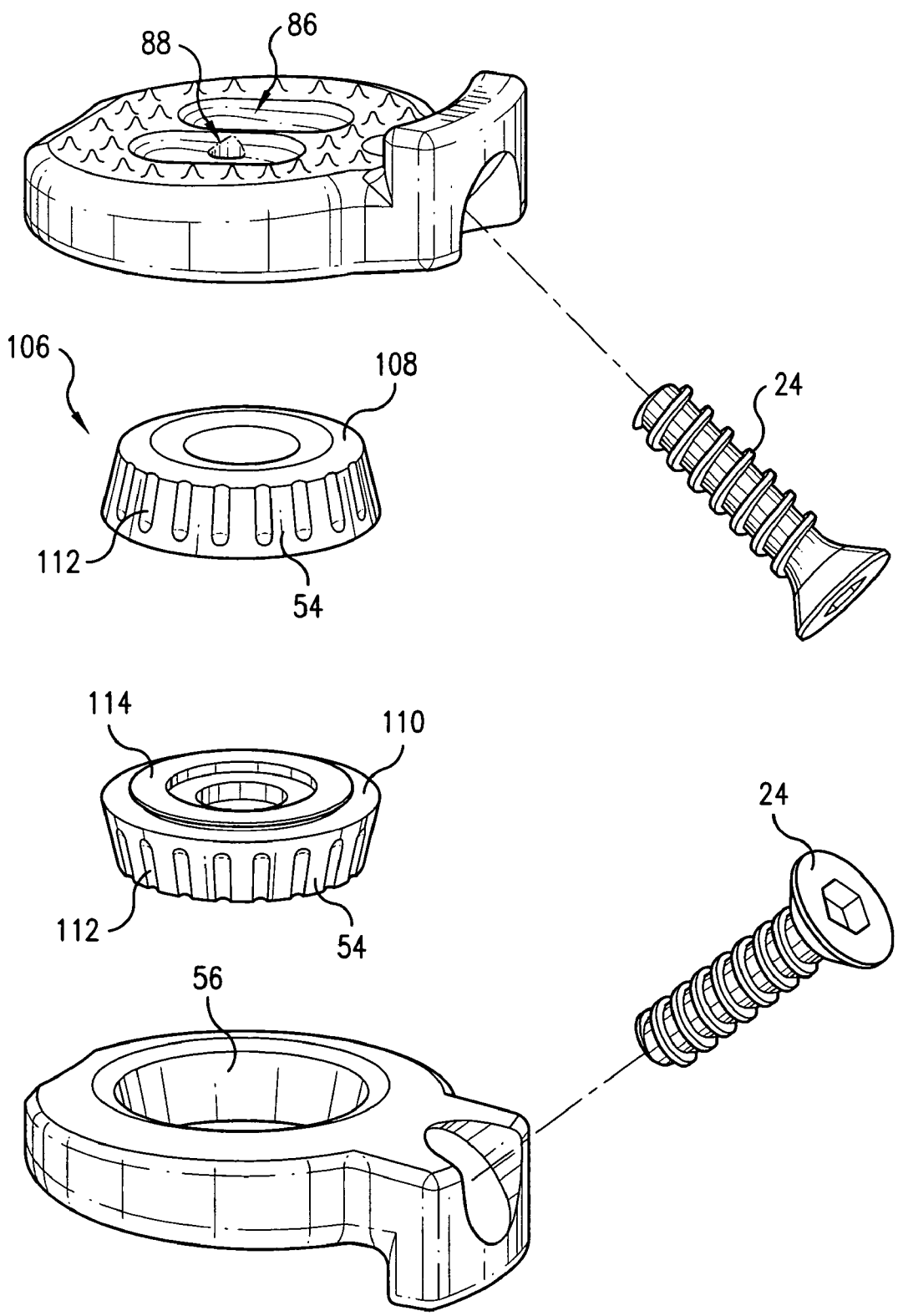
FIGS. 11 and 12 are exploded and perspective views, respectively, of another embodiment of a prosthesis that uses a dovetail configuration for limiting translation between articulation portions, and which has channels to promote lubrication of the articulation.
Figure 12:
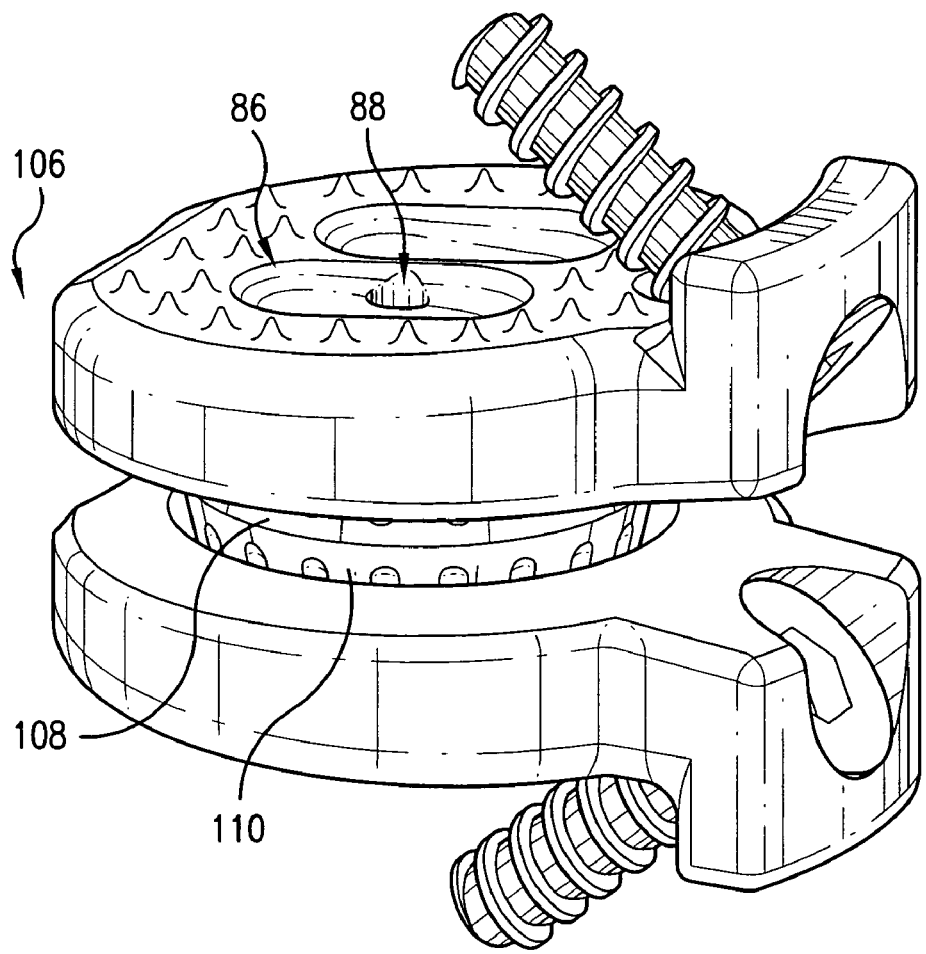
Figure 13:
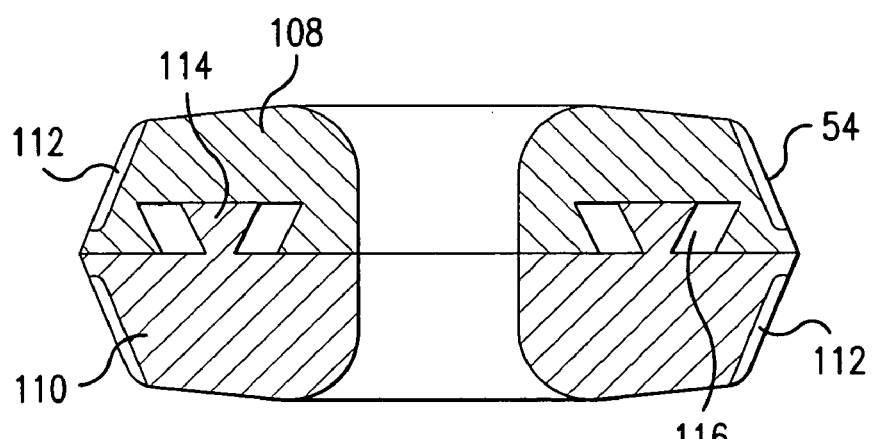
FIG. 13 is a cross-sectional view of the articulation portions thereof.

An embodiment of a prosthesis 106 is shown in FIGS. 11-13, in which the articulation portions 108,110 define exterior lubrication channels 112 to allow human fluid serum to enter and lubricate the bearing surfaces 54,56. In an alternative embodiment, the lubrication channels are provided in the bearing surfaces 56 of the contacting members 118, and the articulation-portion bearing-surfaces 54 are smooth. Additionally, the key 114 and keyway 116 have dovetail cross sections to help retain the articulation portions 108,110 from separating radially or axially at a limit of the translational movement range. In an other embodiment, one of the radial sides of the key 114 and keyway 116 cross-sections can have the respective tapered portion of a partial dovetail cross-sectional shape, and the other radial side can be generally flat or can have a different shape.

Figure 14:
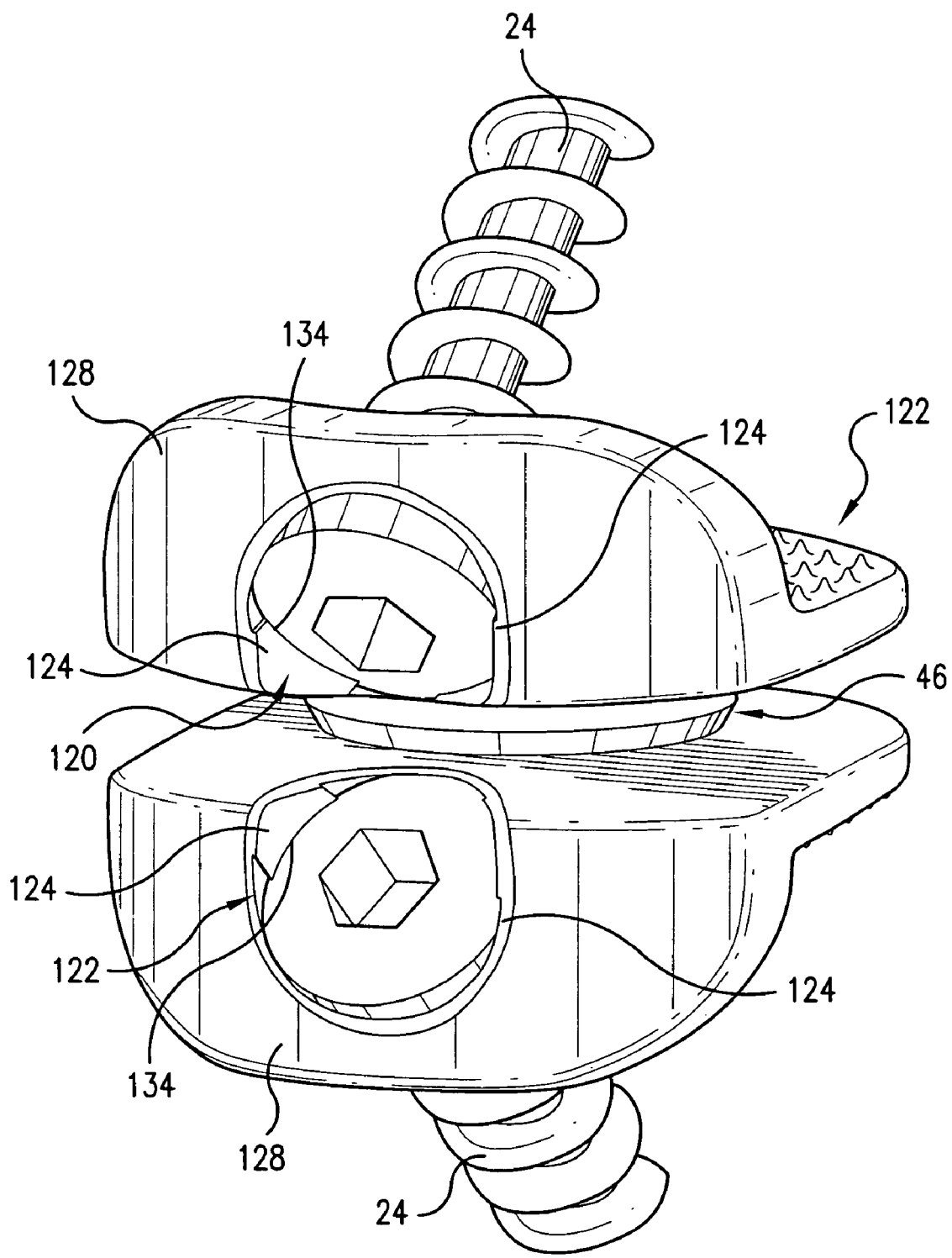
FIG. 14 is an anterior perspective view of a prosthesis embodiment with a fastener-locking mechanism.
Figure 15:
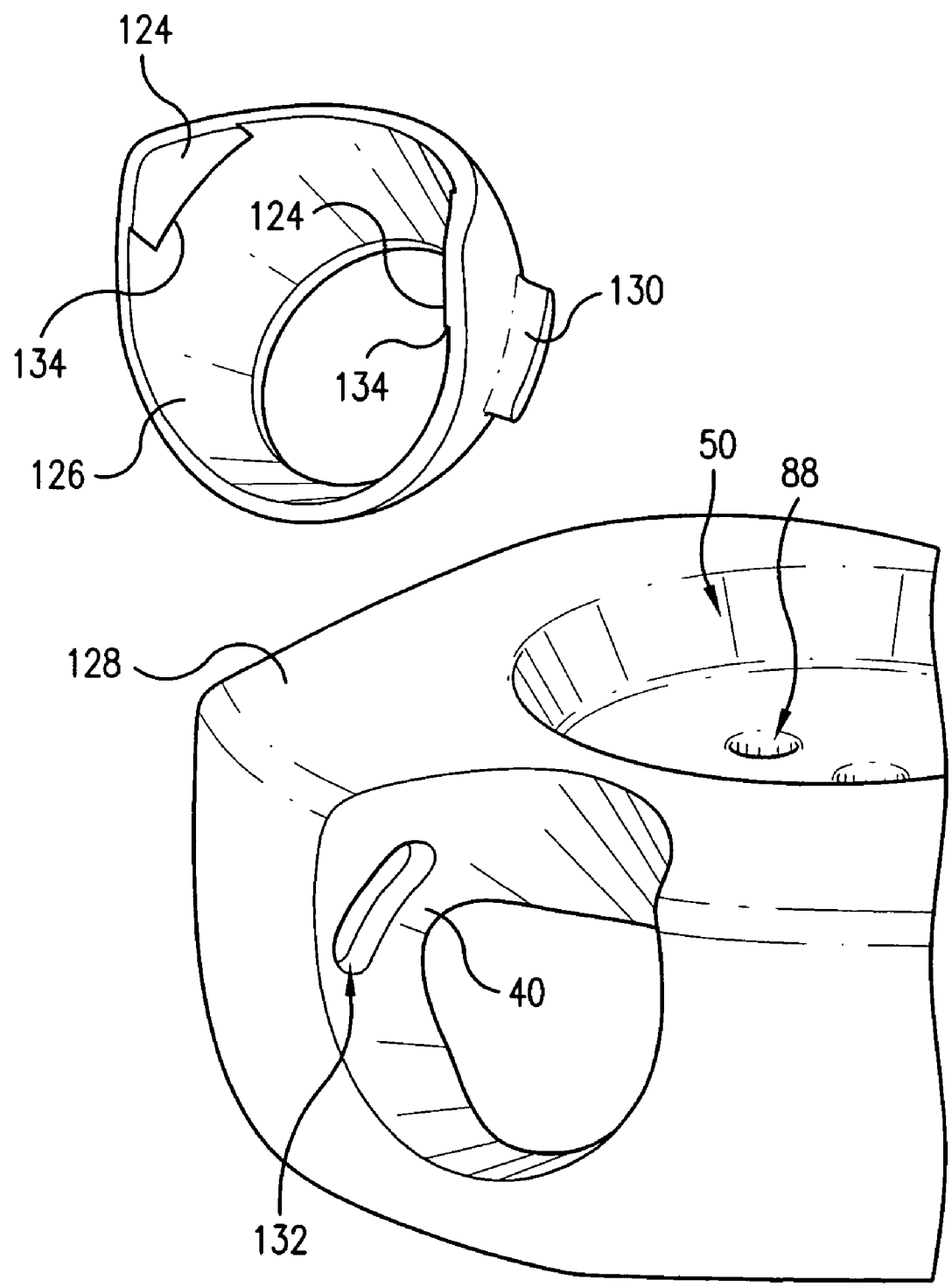
FIG. 15 is an exploded view showing the locking mechanism thereof.
Figure 16C:
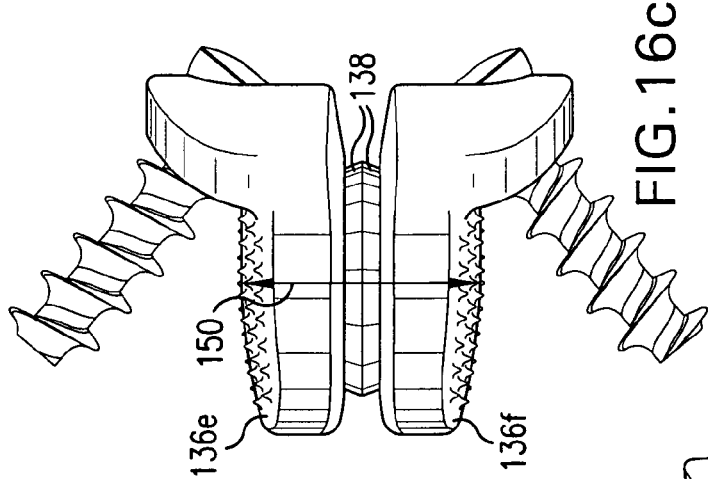
FIGS. 16a-e shows several prostheses that can be assembled from a kit provided in accordance with the present invention.
Figure 16E:
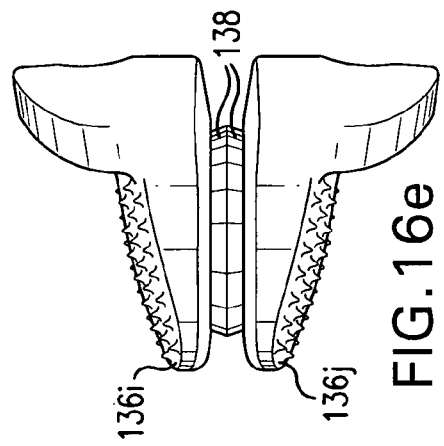
Figure 16B:
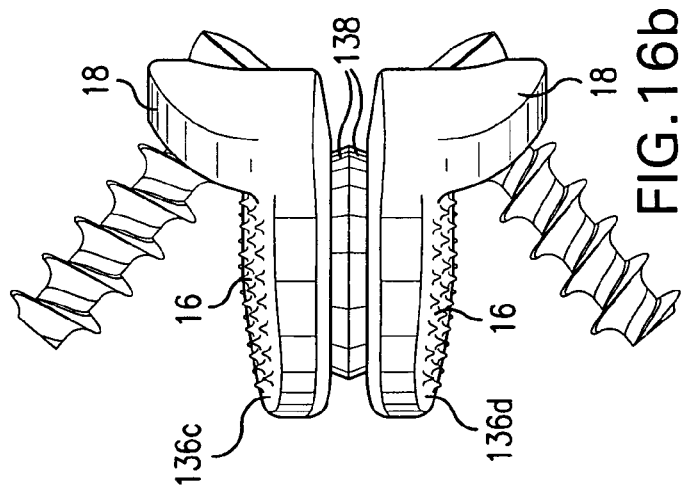
Figure 16A:
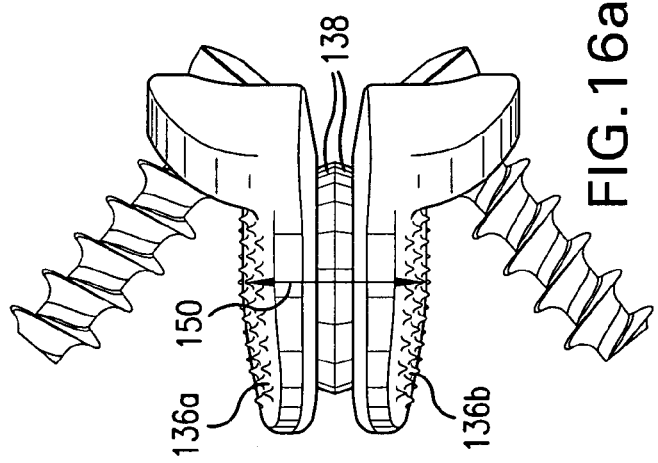
Figure 16D:
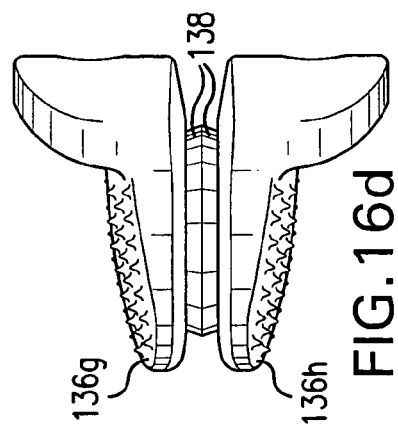

Referring to FIGS. 14 and 15, another embodiment of a prosthesis 122 has a fastener mount portion 120 with a locking element 124. A locking fitting 126 is attached, and preferably fixed, to the contacting members 128, for example via a tongue-in-groove fitting, with a tongue 130 and a grove 132. The fitting 126 includes a locking tab with a ledge 134 that is sufficiently resilient and deformable to allow the head 30 of the fastener 24 to pass thereby when it is screwed into the vertebra. Preferred materials for the construction of the fitting 126 include cobalt chrome and plastics, such as polyethylene and PEEK (polyetheretherketone), or resorbable polymers. A locking ledge that is unitary with the main body of the contacting member can alternatively be used. The ledge 134 blocks retrograde movement of the fastener 24 out of the bone once implanted. Alternative fastener locking devices can be used, such as fasteners with compressible or expanding locking heads.

Figure 17:
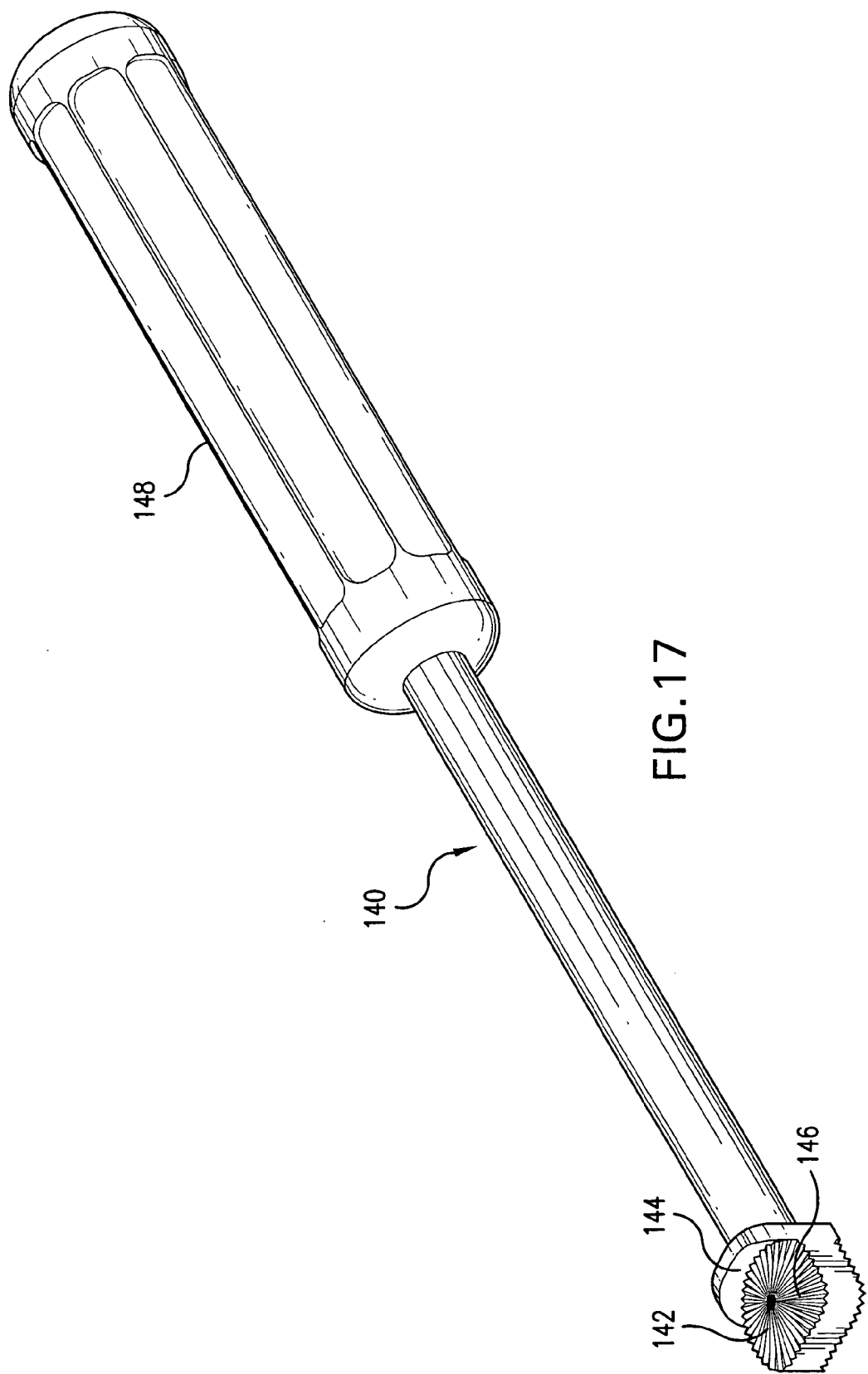
FIG. 17 is a perspective view of an inventive broach configured for determining a desired prosthetic assembly.

A kit is preferably provided to a surgeon with various contacting members 136*a-j* can be provided for assembly about an articulation member that includes articulation portions 138 to provide an assembled prosthesis for implantation. A variety of kit parts allows modularity of prosthetic size to custom fit the device to the patient's evacuated disk space. Examples of prostheses that can be assembled from the kit are shown in FIGS. 16*a-e*. Several broaches such as the broach 140, shown in FIG. 17, can be inserted into the disk space after performing a diskectomy to determine the appropriate height and lordotic angle for the assembled disk prosthesis to be implanted. The broach also distracts the disk space, allowing nerve root decompression and loosening of the ligaments adjacent to the disk space, i.e., annular ligament and posterior longitudinal ligament. The preferred broaches 140 have a probing end 142 that has contacting surfaces in the same general shape as of various assembled prosthesis that can be assembled from the kit parts. A ledge 144 extends adjacent an axial contacting portion 146 to stop the insertion of the probing end 142 at the appropriate location. At the opposite end from the probing tip 142 is a handle 148. Once the proper dimensions of the disk space are determined, contacting members with the desired axial height 150 between the opposed axial contacting surfaces 16 and lordotic angle can be selected to produce the desired configuration in the assembled prosthesis. Preferably, prostheses with axial heights from about 6 mm to about 30 mm, and with between about 0° and 20° of lordosis can be assembled. In the cervical spine, a height of about between 6 mm and 12 mm is preferred. In the thoracic spine, a height of about between 6 mm and 20 mm is preferred. In the lumbar spine, a height of about between 9 mm and 30 mm is preferred.

Figure 18:
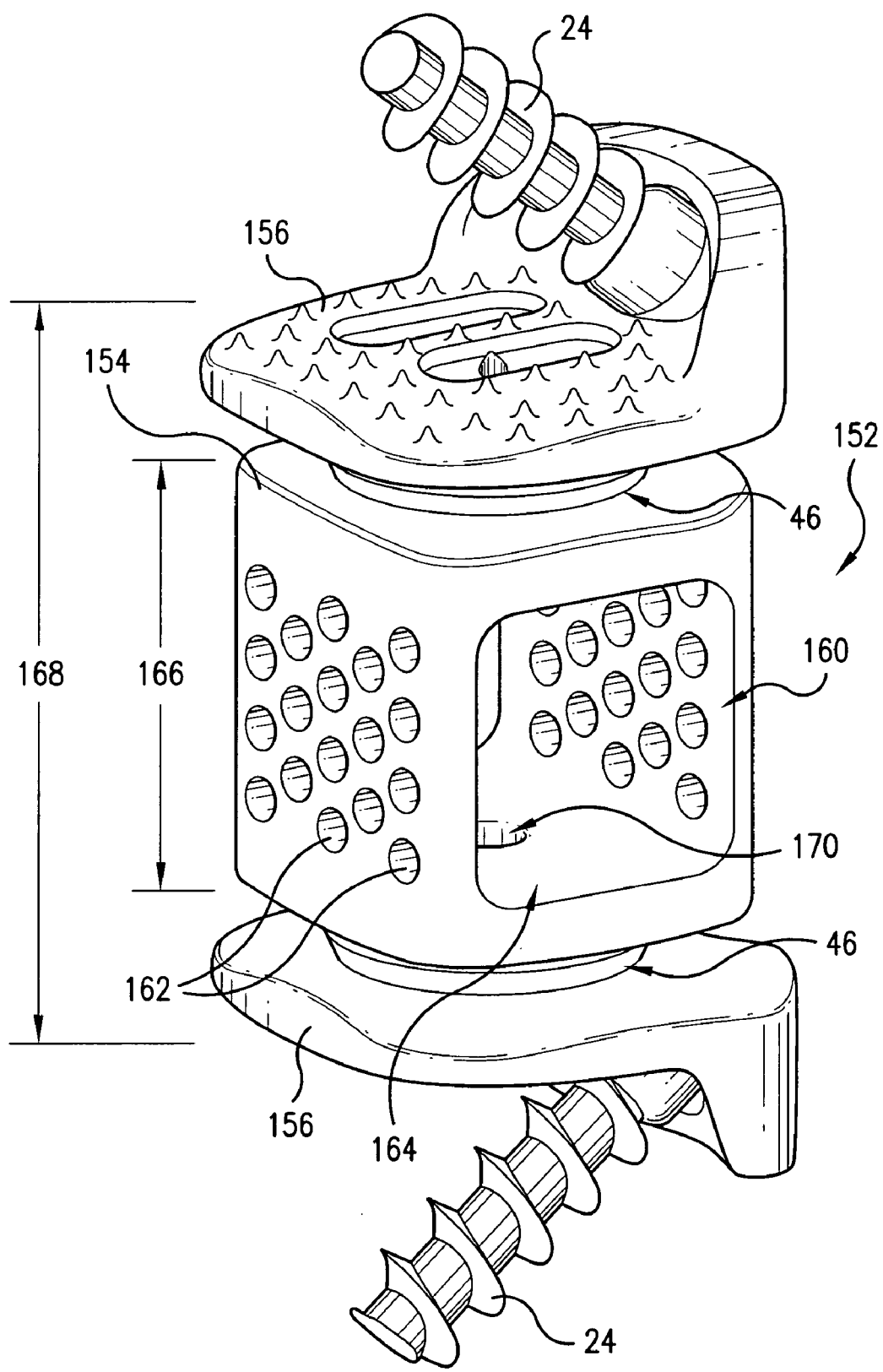
FIGS. 18 and 19 are perspective and exploded views of an embodiment of a prosthesis for use with a corpectomy procedure.
Figure 19:
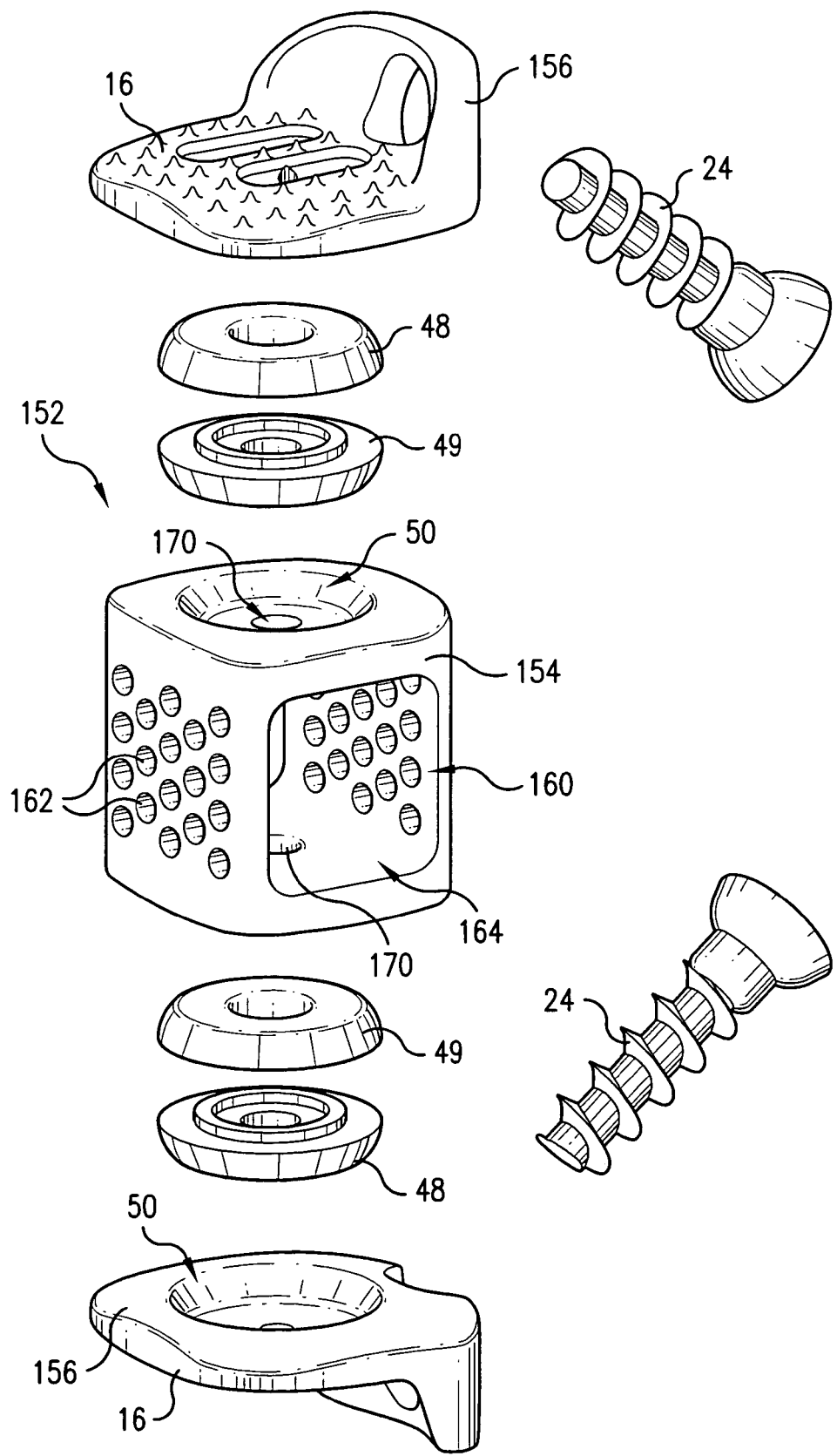

As shown in FIGS. 18 and 19, the embodiment of prosthesis 152 includes a prosthetic vertebral-body portion 154 for use after a corpectomy. Vertebral contacting members 156 are articulated via articulation portions 48,49 to the body portion 154. On an opposite axial side, the body portion 154 is articulably associated with a another vertebral contacting member 156 via a second set of articulation portions 48,49. The body portion 154 defines articular cavities 50 to pivotally and rotatably receive the articulation portions 48 or 49.

The body portion 154 has major and minor openings 160, 162 to promote bone growth and fusion therewith from remaining portions of the vertebra on which the corpectomy has been performed, and into which the body portion is being implanted. The hollow interior 164 of the body portion 154 can be filled with a protein, bone, or other material to further promote the bone growth and fusion. Additionally, suture openings 170 can be provided to thread a suture therethrough or to pass another retaining member between the contacting portions 156 to retain the unit assembled.

The axial height 166 of the body portion 154 is preferably selected to be about the height of a healthy vertebral body or of the vertebral body it replaces, although the body portion height 166 can be made sufficiently larger to position the articulations 46 in the desired position. Preferably, the combined height 168 of the prosthesis 152, measured between the axial contacting surfaces 16 of the contacting members 156 is preferably selected to be about the combined height between the opposed vertebrae that are engaged with the contacting surfaces 16, or of the healthy or desired height of a vertebral body plus the height of a disk on each axial side. Disk heights typically range from about 4 mm to about 20 mm, and vertebra height typically ranges from about 10 mm to 50 mm. The preferred height in the cervical spine is about between 10 mm to 30 mm, in the thoracic spine is about between 20 mm and 60 mm and in the lumbar spine is about between 30 mm and 70 mm. The axial position of the articulations is also preferably selected to provide the desired movement characteristics at the relevant portion of the spine.

Figure 20:
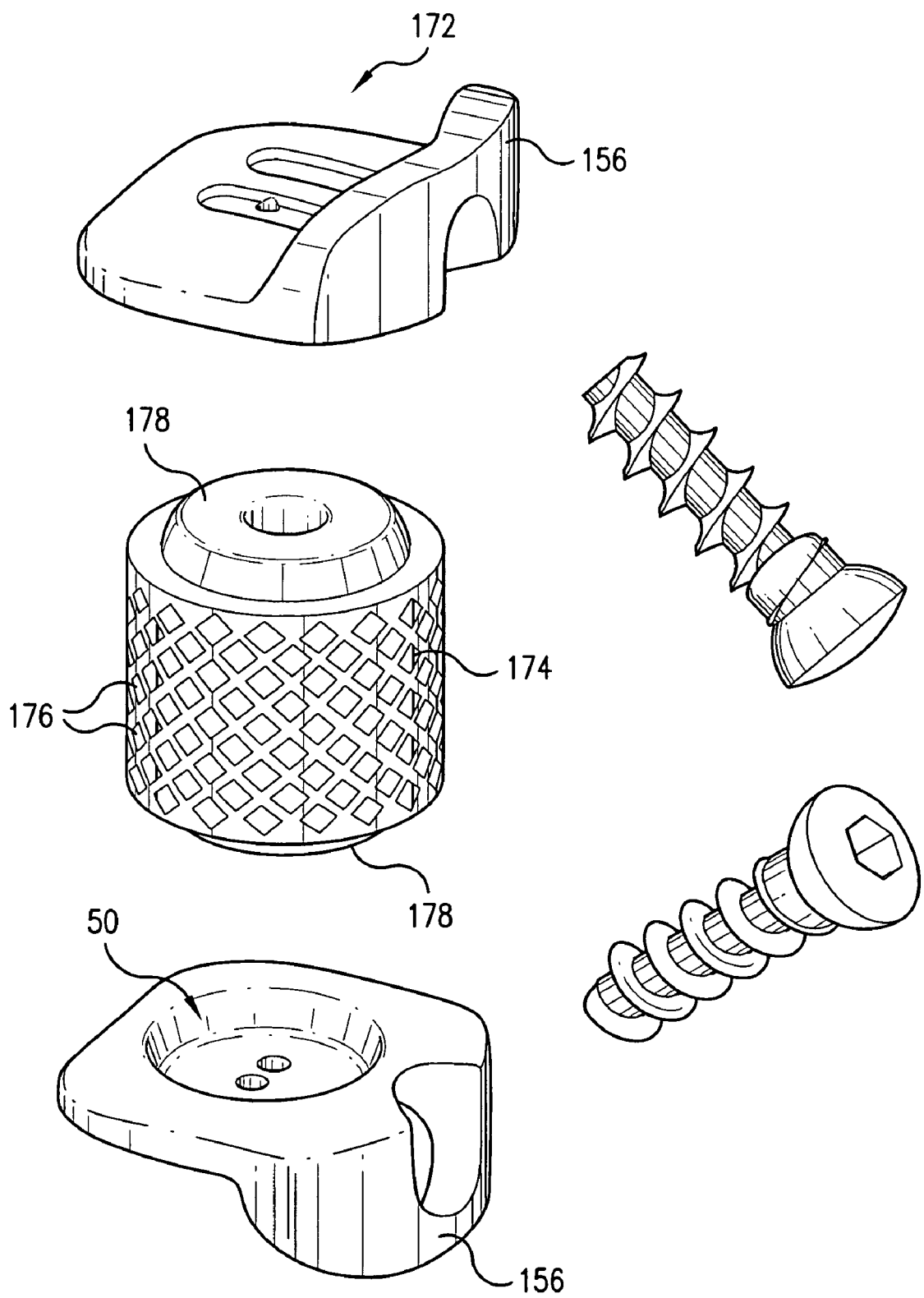
FIG. 20 is an exploded view of another embodiment of a prosthesis for use with a corpectomy procedure.

Referring to FIG. 20, another prosthesis 172 embodiment for use with a corpectomy has a cylindrical body prosthetic portion 174 with angular openings 176 to promote bone fusion. An articulation portion 178 can be of unitary construction with the body portion 174 or otherwise fixed thereto, or can alternatively be slideably associated with the body portion 174, such as by providing a key and keyway translational articulation. The articulation portion is pivotally associated with the contacting members 156. In another embodiment, the body portion has a recess to receive a protrusive articulation portion in fixed association with the contacting member. A membrane 78, as shown in FIGS. 6 and 7 can also be applied to corpectomy orthroplasty embodiments, as well as posts 66.

Substantially the entire prosthesis can be made of a single material to avoid galvanic corrosion or from different materials to take advantage of the different material properties in different parts of the prosthesis. A preferred material for the contacting members, articulation portions, and any present body portion is titanium or another durable and hard material. In one embodiment, the contacting members, articulation portions, and body portion, if employed, are made from a radiolucent material or are otherwise configured to reduce or avoid the production of radio artifacts in an MRI or in an x-ray. As such, the entire device or substantially the entire device can be made of a polymer, such as PEEK. Alternatively, certain portions can be made radiolucent, while others are not. This can be employed to produce better images of the structure of the body without the prosthesis blocking portions of the image. Additionally, radiopaque markers 180, such as shown in FIG. 1, can also be employed in predetermined radiolucent portions of the prosthesis to aid in its imaging, without interfering significantly with the imaging of the surrounding tissue. Preferably, the contacting members, and articulation portions are substantially rigid.

Referring to FIGS. 21-24, the preferred embodiment of an inventive prosthesis insertion device 182 is shown, which functions as a jig to hold an assembled intervertebral prosthesis 10. The insertion device has opposed holding portions 184 that preferably come together along a generally laterally facing vertical surface.

Figure 21:
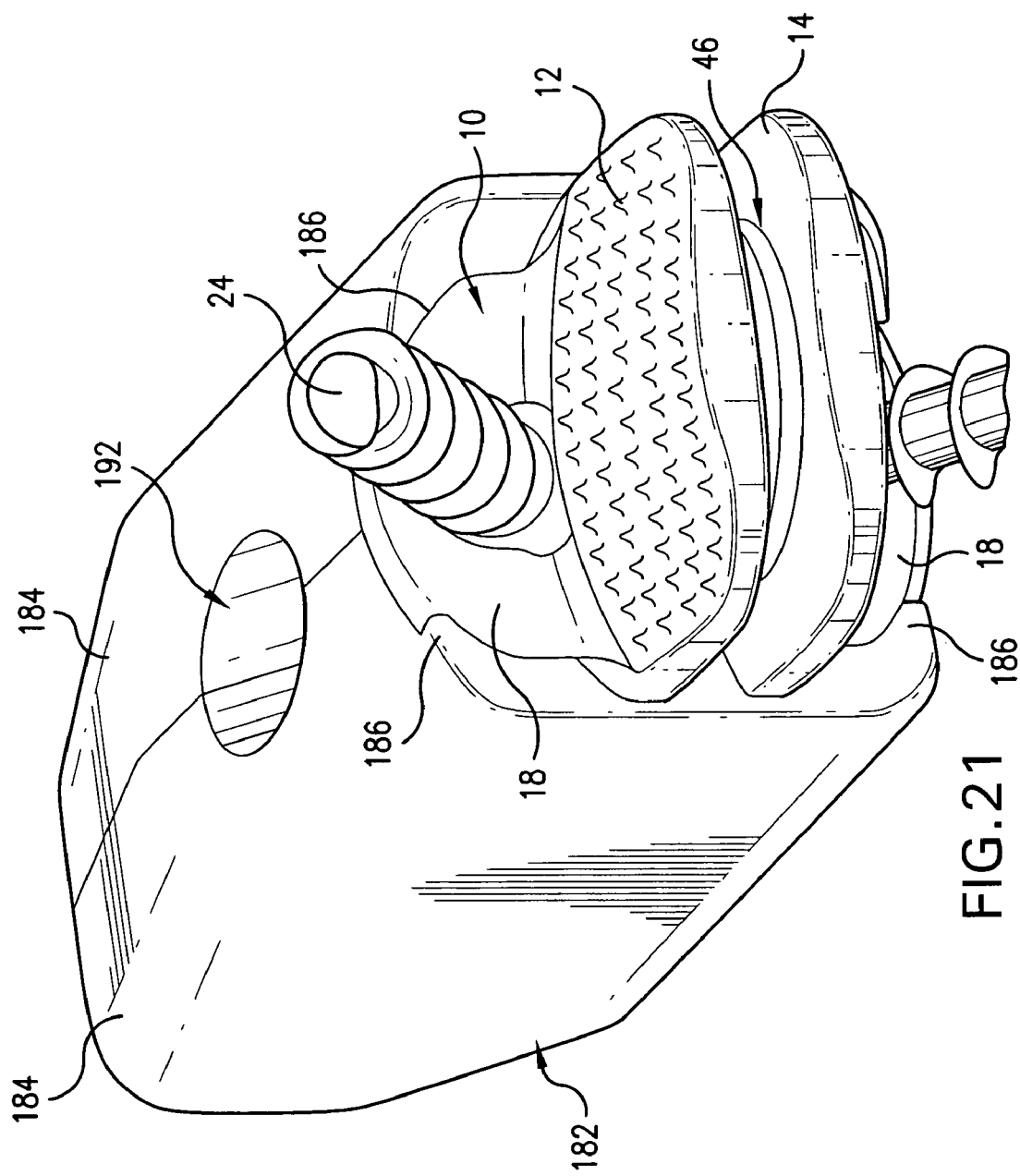
FIG. 21 is a perspective posterior view of an insertion device holding a prosthesis for implantation.

In the holding position of FIG. 21, the holding portions 184 cooperatively and positively hold the prosthesis 10. This is preferably accomplished by the holding portions 184 cooperatively extending around the prosthesis 10 to sufficiently to capture it to inhibit or prevent removal of the prosthesis 10 from the holding portions 184. Extensions 186 extend around the ledges 18, for example, to trap the connecting members against a holding surface 188 that faces the extensions 186. Spacer lips 190 is also preferably provided to fit between the contacting members 12,14 to hold and maintain a predetermined orientation between articulated parts of the prosthesis 10 during implantation.

In the holding position, the holding portions 184 thus block exit of the contacting members 12,14 preferably all directions. The holding portions 184 can be separated, preferably laterally and in an unrestricted manner, to release the prosthesis.

Figure 22:
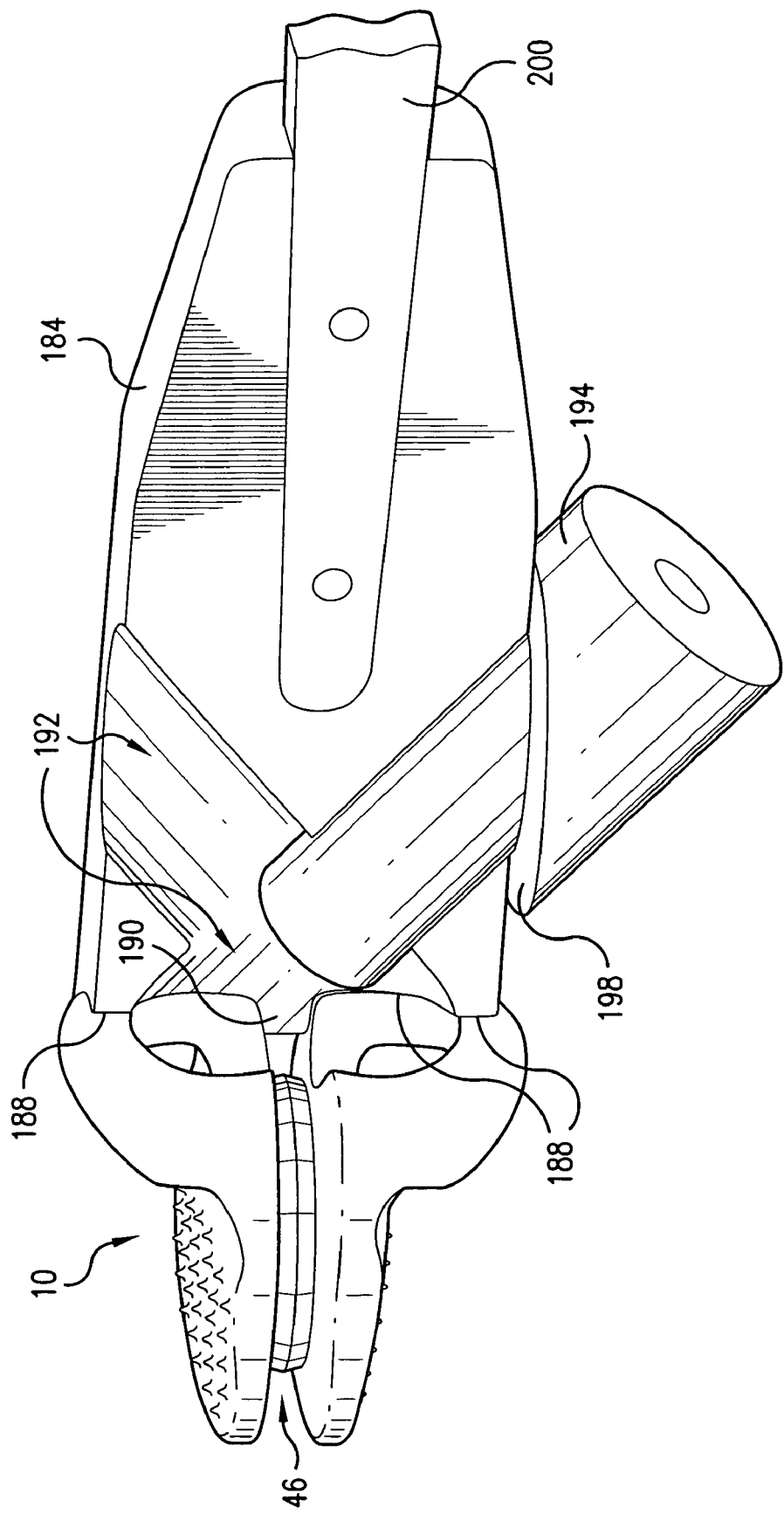
FIGS. 22 and 23 are side views of a holding member of the insertion device, showing the use of a drill guide and a fastener driver, with the opposing holding member of the insertion device not shown for clarity.
Figure 23:
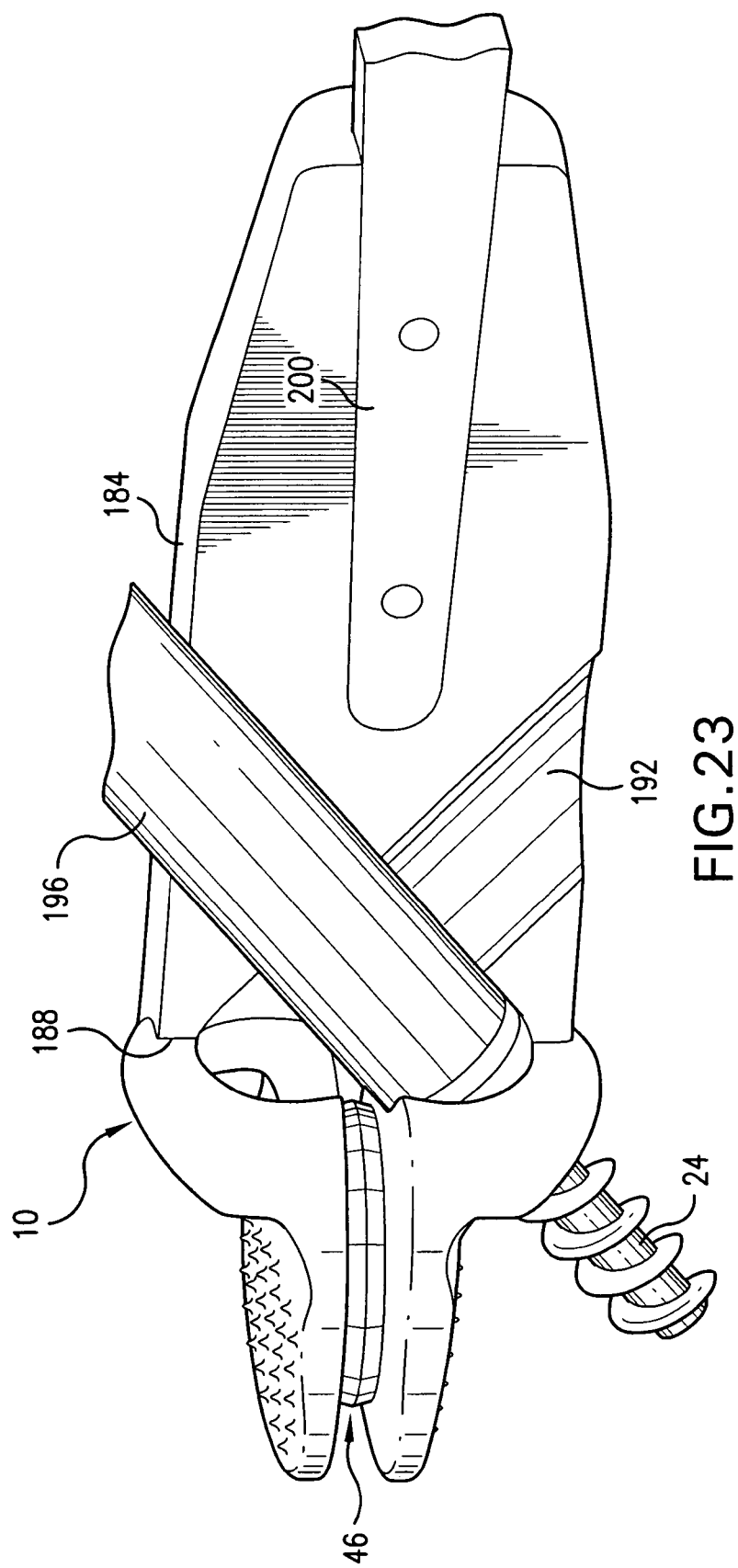

The insertion device preferably also defines bores 192 for receiving and aligning a drill bit or a drill guide 194, as shown in FIG. 22, and the fasteners 24 and fastener driver 196, as shown in FIG. 23, while holding the prosthesis 10 in the desired implantation position in the spine. The drill guide 194 is preferably configured for automatic positioning at a predetermined depth in the bores 192, such as by providing an angled shoulder 198 to abut the outer surface of the holding portions 184.

The bores 192 are preferably defined cooperatively between the holding portions 184 by employing a groove in the inside surface of one holding member 184 that faces a groove in the inside surface of the other holding member 184, but the bores alternatively can extend completely through one of the holding members 184. In addition, the bores 194 for insertion of the diagonally oriented fasteners 24 can cross each other, as can be seen from FIGS. 22 and 23.

Figure 24:
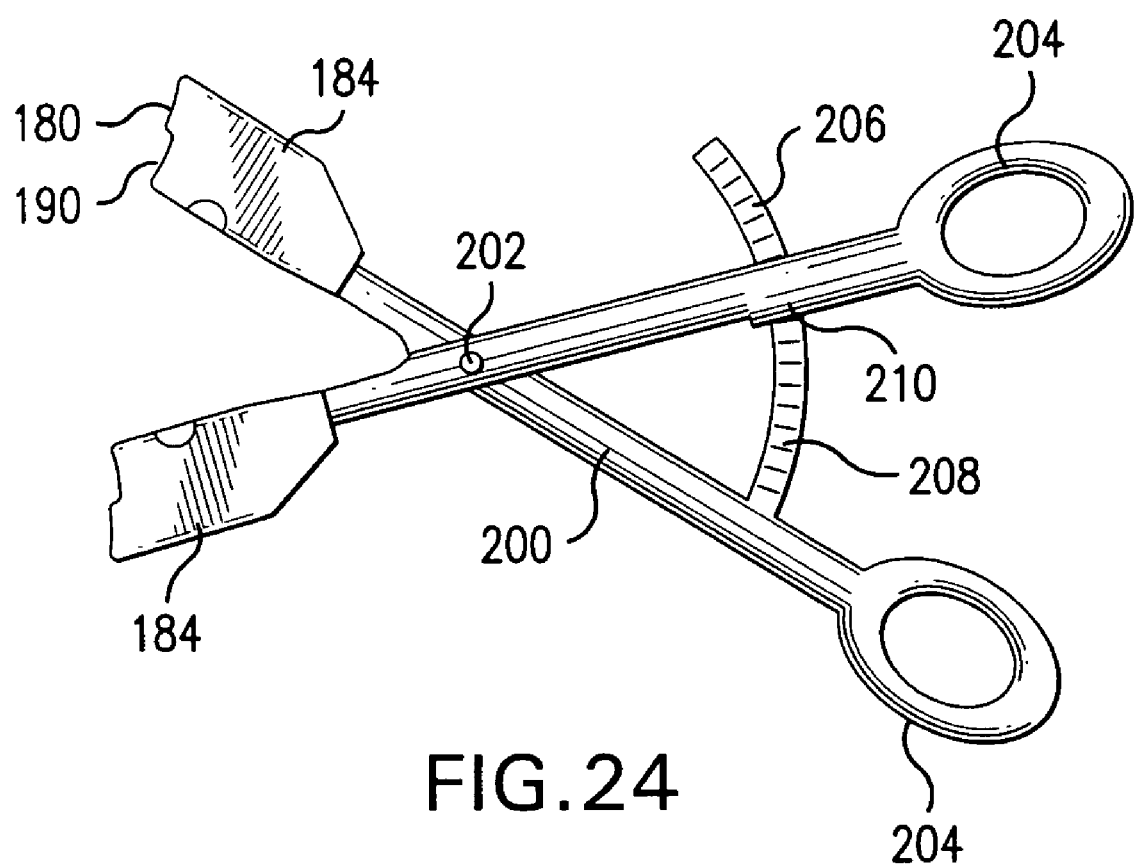
FIG. 24 is a top view of a preferred embodiment of the insertion device.

A connecting member 200 is preferably associated with the holding portions 184 to selectively maintain the holding portions 184 in the holding position and for releasing them therefrom after the implantation. The preferred connecting member 200, shown in FIG. 24, is configured as a forceps with a hinge 202 that pivotally connects the holding portions 184. A scissor linkage with handles 204 hinged at the hinge 202 move the holding portions into and from the holding position. A locking mechanism 206 is provided, such as an actuate arm 208 that extends from one side of the scissor linkage and that has ridges to engage corresponding ridges on the other side 210 of the scissor linkage.

To implant the prosthesis 10 in an endoscopic or laparoscopic procedure, a surgeon preferably performs a disk resection or incises the annulus of the disk to create a window into which the prosthesis 10 can be inserted. The nuclear gelatinous core of the disk is removed, and the faces of the endplates of the vertebral bodies are cleared of cartilage, exposing the cortical bone of the vertebral endplate. The cortex can be breached in the center of the vertebral endplate, exposing cancellous bone.

The surgeon then inserts the prosthesis through an incision with the insertion device 182, preferably in the anterior side of a patient's body. Once the prosthesis 10 is positioned between the vertebrae, the bone is drilled if fasteners are to be used, using a drill guide 194 fitted in the insertion device 182. The fasteners 24 are preferably sequentially inserted into the insertion device 182 and inserted into the bone, such as by rotating with a driver 196 placed in the insertion device 182.

In procedures in which the implantation is not conducted from an anterior side of the spine, contacting members can be used with flanges 18 and fasteners 24 that are oriented an angle between the anterior and lateral sides, for instance. The fasteners can also be offset from the anterior side and can enter the bone at an angle from the anterior-posterior directions, when viewed along the spinal axis.

The preferred arthroplasty prosthesis is tolerant of implantation off-center or out of alignment, as the contacting portions can be self-centering or aligning due to the bias by the ligaments and surrounding soft tissue.

While illustrative embodiments of the invention are disclosed herein, it will be appreciated that numerous modifications and other embodiments may be devised by those skilled in the art. For example, while the preferred embodiments of the invention are described with a configuration for their use between vertebrae, another embodiment can be used at the end of the spine, such as adjacent the skull or between other articulated bones, such as in the appendicular skeleton. The features of different embodiments can be interchanged depending on the desired characteristics of the assembled prosthesis. Therefore, it will be understood that the appended claims are intended to cover all such modifications and embodiments that come within the spirit and scope of the present invention

What is claimed is:

1. An arthroplasty prosthesis, comprising:
    first and second support members configured for cooperatively supporting opposing articulated bones, the first support member having a first at anterior-posterior and lateral pivotal axis, and the second support member having a second anterior-posterior and lateral pivotal axis; and
    first and second articulation portions, the first articulation portion having a first pivotal joint member in pivotal association with the first support member for pivoting at the first pivotal axis, and the second articulation portion having a second pivotal joint member in pivotal association with the second support member for pivoting at the second pivotal axis, wherein the first and second articulation portions are in sliding contact with each other between the first and second pivotal joint members to permit translation of the first and second support members and pivotal joint members with respect to each other,
    wherein the prosthesis is configured such that, when implanted in the spinal column, the articulation portions are disposed in a location corresponding to an intervertebral disk;
    wherein the first and second articulation portions comprise blocking members juxtaposed radially with respect to a spinal axes that extends axially between the support members for abutting each other to limit the translational movement therebetween, and the blocking members comprise:
        a key extending from one of the articulation portions; and
        a keyway defined in the other articulation portion in which the key is received for translational movement, the keyway having an edge wall disposed to block the translational movement of the key.

2. The prosthesis of claim 1, wherein the first and second articulations portions are translatable with respect to each other to translate the first and second support members and pivotal axes with respect to each other substantially uncoupled from pivotal movement of the first and second support members.

3. The prosthesis of claim 1, wherein the first and second pivotal joint members are configured to provide universal pivoting of the first and second support members about the first and second pivotal axes, respectively.

4. The prosthesis of claim 1, wherein the second support member comprises a body prosthetic portion, the prosthesis having an axial height corresponding approximately to the height of a vertebra.

5. The prosthesis of claim 1, wherein one of the first support member and the first articulation portion defines a protrusion extending generally along an axis extending between the support members, and the other defines a recess configured for receiving the protrusion to pivotally associate the first support member and the first articulation portion.

6. The prosthesis of claim 5, wherein one of the second support member and the second articulation portion defines a protrusion, and the other defines a recess configured for receiving the protrusion to pivotally associate the second support member and the second articulation portion.

7. The prosthesis of claim 5, wherein at least one of the recess and protrusion is tapered substantially about a spinal axes that extends axially between the support members.

8. The prosthesis of claim 1, wherein the edge wall and key are annular.

9. The prosthesis of claim 1, wherein the edge wall comprises two edge walls disposed on opposite sides of the keyway such that the key and edge wall concurrently contact at least two locations to block the translational movement of the key within the keyway.

10. The prosthesis of claim 1, wherein the second support member comprises a body prosthetic portion, such that the support members are pivotally and translationally moveable with respect thereto.

11. An arthroplasty prosthesis, comprising:
    first and second support members configured for cooperatively supporting opposing articulated bones, the first support member having a first at anterior-posterior and lateral pivotal axis, and the second support member having a second anterior-posterior and lateral pivotal axis; and
    first and second articulation portions, the first articulation portion having a first pivotal joint member in pivotal association with the first support member for pivoting at the first pivotal axis, and the second articulation portion having a second pivotal joint member in pivotal association with the second support member for pivoting at the second pivotal axis, wherein the first and second articulation portions are in sliding contact with each other between the first and second pivotal joint members to permit translation of the first and second support members and pivotal joint members with respect to each other, wherein the first and second articulation portions are ring shaped with a hollow center,
    wherein the prosthesis is configured such that, when implanted in the spinal column, the articulation portions are disposed in a location corresponding to an intervertebral disk.

12. The prosthesis of claim 11, further comprising a retaining member associated with the support members and extending through the hollow center of the articulation portions to retain the articulation portions in the association with the support members.

13. The prosthesis of claim 12, wherein the retaining member comprises a suture.

14. The prosthesis of claim 11, wherein at least one of the support members comprises a post extending into the hollow center of at least one of the articulation portions for retaining the at least one articulation portion in said association with the support member associated therewith.

15. The prosthesis of claim 11, wherein the first support member comprises a first bone contacting member configured for engaging first vertebra of the spinal column, the first contacting member comprising:
    a fastener mount portion configured for attaching a bone fastener thereto; and
    vertebral contacting surfaces disposed and oriented for positioning an apophyseal ring of the first bone with respect to the fastener mount portion in an attachment position for attaching the fastener from the fastener mount portion through the apophyseal ring to attach the first contacting member to the first bone.

16. The prosthesis of claim 15, wherein the fastener mount portion defines an opening for receiving a threaded surgical fastener therethrough.

17. The prosthesis of claim 16, wherein the fastener mount portion is oriented for inserting the fastener diagonally into the apophyseal ring.

18. The prosthesis of claim 15, wherein the vertebral contacting surfaces are oriented to capture axial and radial surfaces of the vertebral body for positioning the apophyseal ring in the attachment position.

19. The prosthesis of claim 11, wherein the opposing articulated bones comprise first and second vertebra bodies, each having a respective apophyseal ring, and wherein the first and second support members comprise:
- an axial contacting surface oriented to abut and support an axial face of a respective one of the first and second vertebra bodies;
- a radial contacting surface configured to abut a radial side of the respective one of the first and second vertebra bodies; and
- an apophysis receiving area between the axial and radial contacting surfaces defining an apophysis groove that is disposed and configured for receiving the apophyseal ring of the respective one of the first and second vertebra bodies.

20. The prosthesis of claim 11, wherein at least one of the support members is made of a radiolucent material such that the visibility of the prosthesis during X-ray, M.R.I. or C.T. scan is reduced.

21. The prosthesis of claim 20, wherein the support members comprise radiopaque marks visible in an MRI, CT scan, or x-ray.

22. The prosthesis of claim 20, wherein each of the support members is substantially radiolucent.

23. The prosthesis of claim 11, wherein at least one of the support members has and is configured to deliver an antibiotic, protein, or biologically active substance to the implantation site.

24. The prosthesis of claim 11, wherein both of the support members are configured for engaging a respective axial skeleton bone adjacent the implantation site.

25. The prosthesis of claim 11, wherein the second pivotal axis comprises an upper body anterior-posterior and lateral pivotal axis of the second support member, and the second support member comprises a third pivotal axis comprising a lower body anterior-posterior and lateral pivotal axis of the second support member.

26. The prosthesis of claim 25, further comprising:
- a third support member having a fourth anterior-posterior and lateral pivotal axis;
- a second articulation member, including:
    - a third articulation portion having a third pivotal joint member in pivotal association with the second support member for pivoting at the third pivotal axis, and
    - a fourth articulation portion having a fourth pivotal joint member in pivotal association with the third support member for pivoting at the fourth pivotal axis.

27. The prosthesis of claim 26, wherein the third support member comprises a vertebral contacting member.

28. The prosthesis of claim 27, wherein the third and fourth articulation portions are translatable with respect to each other at a location between the third and fourth joint members to translate the second and third support members and pivotal axes with respect to each other.

29. The prosthesis of claim 11, wherein the first and second articulation portions are in sliding contact against each other to allow the translation.

\* \* \* \* \*